(12) United States Patent
Stringer et al.

(10) Patent No.: US 10,973,586 B2
(45) Date of Patent: Apr. 13, 2021

(54) SYSTEMS AND METHODS OF DETERMINING ONE OR MORE PROPERTIES OF A CATHETER AND A DISTAL TIP THEREOF

(71) Applicant: Verum TCS, LLC, Salt Lake City, UT (US)

(72) Inventors: Bradley J. Stringer, Kaysville, UT (US); Spencer B. Shumway, South Jordan, UT (US); Matthew D. Holbrook, Durham, NC (US)

(73) Assignee: Verum TCS, LLC, Salt Lake City, UT (US)

(*) Notice: Subject to any disclaimer, the term of this patent is extended or adjusted under 35 U.S.C. 154(b) by 783 days.

(21) Appl. No.: 15/408,235

(22) Filed: Jan. 17, 2017

(65) Prior Publication Data

US 2017/0224420 A1    Aug. 10, 2017

Related U.S. Application Data

(60) Provisional application No. 62/355,261, filed on Jun. 27, 2016, provisional application No. 62/321,610, (Continued)

(51) Int. Cl.
*A61B 34/20* (2016.01)
*A61B 5/1459* (2006.01)
(Continued)

(52) U.S. Cl.
CPC .............. *A61B 34/20* (2016.02); *A61B 1/063* (2013.01); *A61B 1/0669* (2013.01); *A61B 1/07* (2013.01);
(Continued)

(58) Field of Classification Search
CPC ............ A61B 34/20; A61B 2034/2051; A61B 5/6852; A61B 18/22; A61B 18/24;
(Continued)

(56) References Cited

U.S. PATENT DOCUMENTS

| 5,995,208 A | 11/1999 | Sarge et al. |
| 6,178,346 B1 | 1/2001 | Amundson et al. |

(Continued)

FOREIGN PATENT DOCUMENTS

WO    2007064746 A1    6/2007

OTHER PUBLICATIONS

Ahn, Daniel H. et al., Upper Extremity Venous Thrombosis in Patients With Cancer With Peripherally Inserted central Venous Catheters: A Retrospective Analysis of Risk Factors, Journal of Oncology Practice, Jan. 2013, pp. e8-e12, vol. 9, Issue 1, American Society of Clinical Oncology.

(Continued)

*Primary Examiner* — Deborah L Malamud
(74) *Attorney, Agent, or Firm* — Woodard Emhardt Henry Reeves & Wagner LLP

(57) ABSTRACT

Tip confirmation systems and related methods are disclosed. A method of determining one or more properties of a catheter in a patient comprises advancing a catheter in vasculature of a patient, the catheter coupled to at least one radiation source and at least one detector, transmitting source electromagnetic radiation from the at least one radiation source out of the catheter proximate a distal tip thereof, measuring an intensity of backscattered electromagnetic radiation from the at least one radiation source with the at least one detector, and providing a signal indicative of a location of the distal tip within the vasculature based, at least (Continued)

in part, on the measured intensity of the backscattered electromagnetic radiation. Related systems and methods are also disclosed.

16 Claims, 15 Drawing Sheets

Related U.S. Application Data filed on Apr. 12, 2016, provisional application No. 62/312,360, filed on Mar. 23, 2016, provisional application No. 62/280,559, filed on Jan. 19, 2016.

(51) Int. Cl.

| | |
|---|---|
| *A61B 5/107* | (2006.01) |
| *A61B 5/00* | (2006.01) |
| *A61B 1/06* | (2006.01) |
| *A61B 1/07* | (2006.01) |
| *A61M 25/01* | (2006.01) |
| *A61B 90/00* | (2016.01) |

(52) U.S. Cl.
CPC .......... *A61B 5/0059* (2013.01); *A61B 5/0084* (2013.01); *A61B 5/1076* (2013.01); *A61B 5/1459* (2013.01); *A61M 25/0105* (2013.01); *A61B 2034/2055* (2016.02); *A61B 2090/3945* (2016.02); *A61B 2090/3979* (2016.02); *A61M 2025/0166* (2013.01)

(58) Field of Classification Search
CPC ...... A61B 2018/1861; A61B 2034/107; A61B 2034/2055; A61B 2034/301; A61B 18/18; A61B 2034/2065; A61B 2034/303; A61B 2090/364; A61B 2576/00; A61B 5/0031; A61B 2018/00636; A61B 2018/00642; A61B 5/6886; A61N 1/05; A61N 1/36; A61N 1/00; A61N 1/08; A61N 1/18; A61N 1/36185; A61N 1/372; A61N 1/37223; G06T 7/0012; G06T 2207/30101

See application file for complete search history.

(56) References Cited

U.S. PATENT DOCUMENTS

| | | | |
|---|---|---|---|
| 6,366,726 B1 | 4/2002 | Wach et al. | |
| 6,999,809 B2 | 2/2006 | Currier et al. | |
| 7,392,707 B2 | 7/2008 | Wong et al. | |
| 8,027,714 B2 * | 9/2011 | Shachar | A61B 5/062 |
| | | | 600/409 |
| 2003/0092995 A1 | 5/2003 | Thompson | |
| 2007/0016072 A1 | 1/2007 | Grunwald et al. | |
| 2007/0197919 A1 | 8/2007 | Krisch et al. | |
| 2008/0039715 A1 | 2/2008 | Wilson et al. | |
| 2009/0227952 A1 | 9/2009 | Blakstvedt et al. | |
| 2011/0004059 A1 | 1/2011 | Arneson et al. | |
| 2014/0236024 A1 | 8/2014 | Bierhoff et al. | |
| 2014/0276108 A1 | 9/2014 | Vertikov et al. | |
| 2015/0080688 A1 | 3/2015 | Cinbis et al. | |

OTHER PUBLICATIONS

Blackwood, Brian P. et al., Peripherally Inserted Central Catheters Complicated by Vascular Erosion in Neonates, Joural of Parenteral Enteral Nutrition, Aug. 2016, pp. 890-895, Sage Publishing.
Cadman A., et al., To clot or not to clot? That is the question in central venous catheters, The Royal College of Radiologist, 2004, pp. 349-355, Elsevier Ltd.
Caers, Jo et al., Catheter tip position as a risk factor for thrombosis associated with the use of subcutaneous infusion ports, 2004, pp. 325-331, Springer-Verlag.
Chopra, Vineet et al., The Michigan Appropriateness Guide for Intravenous Catheters (MAGIC): Results From a Multispecialty Panel Using the RAND/UCLA Appropriateness Method, Annals of Internal Medicine, Sep. 15, 2015, pp. S1-S39, vol. 163, No. 6 (Supplemental).
Chu, Koung-Shing et al., Accurate Central Venous Port—A Catheter Placement: Intravenous Electrocardiography and Surface Landmark Techniques Compared by Using Transesophageal Echocardiography, 2004, pp. 910-914, International Anesthesia Research Society.
Wikimedia Commons, PICC Catheter, https://commons.wikimedia.org/wiki/File:Blausen_0193Catheter_PICC.png, visited Feb. 9, 2017, 3 pages.
Fletcher S.J. et al., Editorial I-Metabolic support of critically ill patients: parenteral nutrition to immunonutrition; Editorial II—Safe placement of central venous catheters: where should the tip of the catheter lie?, British Journal of Anaesthesia, Aug. 2000, pp. 185-191, vol. 85, No. 2.
Fricke, Bradley L., et al., Placement of Peripherally Inserted Central Catheters without Fluoroscopy in Children: Initial Catheter Tip Position, Mar. 2005, pp. 887-892, RSNA.
Girgenti, Constance et al., Successfully Eliminating Chest Radiography by Replacing It With Dual Vector Technology and an Algorithm for PICC Placement, 2014, pp. 71-74, vol. 19, No. 2, Elsevier Inc.
Harako, Michelle E. et al., Optimizing the patient positioning for PICC line tip determination, Emergency Radiology, 2003, pp. 186-189, ASER.
Hostetter, Russell, Ph.D., et al. Precision in Central Venous Catheter Tip Placement: A Review of the Literature, 2010, 10 pgs., vol. 15, No. 3.
Jacques, Steven L., Corrigendum: Optical properties of biological tissues: a review, Physics in Medicine and Biology, Jun. 2013, 28 pgs., IOP Publishing.
Lafortune, Sue, The Use of Confirming X-Rays to Verify Tip Position for Peripherally Inserted Catheters, Journal of Intravenous Nursing, Jul./Aug. 1993, pp. 246-250, vol. 16, No. 4.
Lelovas, Pavlos P. et al., A Comparative Anatomic and Physiologic Overview of the Porcine Heart, Journal of the American Association for Laboratory Animal Science, Sep. 2014, pp. 432-438, vol. 53, No. 5.
Loughran, Stephen C., et al., Peripherally Inserted Central Catheters: A Report of 2506 Catheter Days, Journal of Parenteral and Enteral Nutrition, 1994, pp. 133-136, vol. 19, No. 2.
Moureau, Nancy L. et al., Electrocardiogram (EKG) Guided Peripherally Inserted Central Catheter Placement and Tip Position: Results of a Trial to Replace Radiological Confirmation, 2010, pp. 8-14, vol. 15, No. 1.
Niakazawa, Nadine, Challenges in the Accurate Identification of the Ideal Catheter Tip Location, The 2010 Suzanne LaVere Herbst Award Lecture, 2010, pp. 196-201, vol. 15, No. 4.
Pittiruti, Mauro et al., The EKG Method for Positioning the Tip of PICCs: Results form Two Preliminary Studies, 2010, pp. 179-186, vol. 13, No. 4.
Scott, Walter L., CPAT, PhD, Central Venous Catheters An Overview of Food and Durg Administration Activities, Vascular Access in the Oncology Patient, Jul. 1995, pp. 377-391, vol. 4, No. 3.
Vesely, Thomas M., Central Venous Catheter Tip Position: A Continuing Controversy, May 2003, pp. 527-534.
Yue, Zy, et al., Complications with peripherally inserted central catheters—observations and nursing experiences at one medical center in Chengdu, Hu li za zhi The Journal of Nursing, 2010, http://europepmc.org/abstract/med/20535681, visited Feb. 3, 2017, 2 pages.
Tuchin, Valery, Chapter 1: Optical Properties of Tissues with Strong (Multiple) Scattering, Tissue Optics Light Scattering Methods and Instruments for Medical Diagnostics, 2015, pp. 3-53, Third Edition, SPIE, Bellingham, Washington.
Tuchin, Valery, Chapter 7: Methods and Algorithms for Measurement of the Optical Parameters of Tissues, Tissue Optics Light

(56) References Cited

OTHER PUBLICATIONS

Scattering Methods and Instruments for Medical Diagnostics, 2015, pp. 245-357 Third Edition, SPIE, Bellingham, Washington.

Tuchin, Valery, Chapter 9: Controlling Optical Properties of Tissue, Tissue Optics Light Scattering Methods and Instruments for Medical Diagnostics, 2015, pp. 419-590, Third Edition, SPIE, Bellingham, Washington.

Tuchin, Valery, Chapter 10: Continuous Wave Spectrophotometry and Imaging, Tissue Optics Light Scattering Methods and Instruments for Medical Diagnostics, 2015, pp. 593-603, Third Edition, SPIE, Bellingham, Washington.

* cited by examiner

SYSTEMS AND METHODS OF DETERMINING ONE OR MORE PROPERTIES OF A CATHETER AND A DISTAL TIP THEREOF

CROSS-REFERENCE TO RELATED APPLICATIONS

This application claims the benefit of U.S. Provisional Patent Application Ser. No. 62/355,261, filed Jun. 27, 2016, and entitled "SYSTEMS AND METHODS OF DETERMINING A LOCATION OF A CATHETER AND A DISTAL TIP THEREOF," of U.S. Provisional Patent Application Ser. No. 62/321,610, filed Apr. 12, 2016, and entitled "SYSTEMS AND METHODS OF DETERMINING A LOCATION OF A CATHETER AND A DISTAL TIP THEREOF," of U.S. Provisional Patent Application Ser. No. 62/312,360, filed Mar. 23, 2016, and entitled "SYSTEMS AND METHODS OF DETERMINING A LOCATION OF A DISTAL TIP OF A CATHETER," and of U.S. Provisional Patent Application Ser. No. 62/280,559, filed Jan. 19, 2016, and entitled "SYSTEMS AND METHODS OF DETERMINING A LOCATION OF A DISTAL TIP OF A CATHETER," the disclosure of each of which applications is hereby incorporated herein in their entirety by this reference.

TECHNICAL FIELD

Embodiments of the disclosure relate generally to tip confirmation systems (TCSs) for determining one or more properties, such as a location, of a distal tip of a catheter in the vasculature of a patient, methods of advancing a catheter and monitoring the advancement of the catheter in a patient, and related methods. More particularly, embodiments of the disclosure relate to systems and methods for determining when a distal tip of a catheter approaches the cavoatrial junction of a patient during placement of the catheter, systems and methods for tracking the catheter during insertion thereof and a direction of advancement thereof, and methods and systems for determining a diameter, a cross-sectional area, or both of the vasculature of the patient.

BACKGROUND

Peripherally inserted central catheters (PICCs) (also referred to as percutaneous indwelling catheters) are a form of central venous catheters (CVCs) that may be used to deliver antibiotics, chemotherapy (e.g., for oncolytic therapy), nutrition, etc., to a patient for a prolonged period of time, such as for days, weeks, or even months. A PICC may generally be inserted into a peripheral vein in a patient's arm, and then advanced through increasingly larger veins to a location suitable to deliver medicaments to the patient. In general, it is desired to position the PICC such that a distal tip thereof is located proximate the cavoatrial junction (CAJ), which is where the superior vena cava (SVC) meets the right atrium of the heart. The PICC is most effective when the distal tip is placed at or within about 5 mm to about 10 mm of the CAJ (e.g., in a direction toward the superior vena cava).

However, placement of the distal tip of a PICC proximate the cavoatrial junction requires a high degree of precision and usually requires a trained clinician, nurse, or practitioner. If the distal tip of the PICC is advanced too far, the tip may contact the wall of the heart (e.g., such as in the right atrium), damaging the wall and potentially causing an irregular heartbeat, such as an arrhythmia or tachycardia. Alternatively, if the tip is not advanced far enough and remains in a vein, the patient may be exposed to an increased risk of thrombosis, spontaneous malposition, or catheter dysfunction. In some instances, the medicaments may not be sufficiently diluted and transferred through the body, which may cause damage to locations of the vasculature and tissue where too high a concentration of medicaments are present (e.g., as in intravenous extravasation). Further, during advancement of the PICC, the distal tip thereof may undesirably deviate from a desired path in the patient's vasculature. For example, in as many as about 10 percent of adult patients and about 25 percent of pediatric patients, the distal tip of the catheter may deviate from the desired path at the innominate junction or other junctions of the vasculature between an insertion point and the CAJ. When the distal tip deviates from an intended course, the clinician may at least partially retract and refeed the PICC in an effort to place the PICC in a desired location.

PICCs are generally placed using tip confirmation systems (TCSs) that employ radiography techniques. Conventional tip confirmation systems include the use of fluoroscopic dyes and fluoroscopy or x-rays. However, the use of such systems requires specialized dyes and equipment and exposes the patient to harmful ionizing radiation.

BRIEF SUMMARY

Embodiments disclosed herein include methods and systems of determining one or more properties, such as a location, of a distal tip of a catheter relative to a cavoatrial junction. For example, in accordance with one embodiment, a method of determining a location of a distal tip of a catheter comprises advancing a catheter in a vein of a patient, the catheter comprising a fiber optic cable comprising at least one optical fiber coupled to a radiation source and a detector at a proximal end thereof, transmitting source electromagnetic radiation having at least a first substantially monochromatic wavelength and electromagnetic radiation having at least a second substantially monochromatic wavelength from the radiation source to a distal end of the at least one optical fiber, measuring an intensity of backscattered electromagnetic radiation at the at least a first substantially monochromatic wavelength and at the at least a second substantially monochromatic wavelength, determining a ratio of the intensity of the backscattered electromagnetic radiation at the at least a first substantially monochromatic wavelength to the intensity of the backscattered electromagnetic radiation at the at least a second substantially monochromatic wavelength, and determining a location of a distal tip of the catheter based on a value of the ratio.

In additional embodiments, a system for determining a location of a catheter within a patient comprises at least one optical fiber extending from a proximal end of a catheter to a distal tip of the catheter, a radiation source operably coupled to a proximal end of the at least one optical fiber and configured to transmit source electromagnetic radiation comprising at least a first substantially monochromatic wavelength and at least a second substantially monochromatic wavelength through the at least one optical fiber to a distal tip thereof, a detector operably coupled to the proximal end of the at least one optical fiber and configured to measure an intensity of backscattered electromagnetic radiation at the at least a first substantially monochromatic wavelength and at the at least a second substantially monochromatic wavelength received at the distal tip of the at least one optical fiber, and a computing system configured to calculate a ratio of the intensity of the backscattered electromagnetic radiation at the at least a first substantially monochromatic wavelength to the intensity of the backscattered electromagnetic radiation at the at least a second substantially monochromatic wavelength.

In further embodiments, a method of determining a location of a distal tip of a catheter comprises advancing a catheter in a vein of a patient, the catheter comprising a fiber optic cable comprising a single optical fiber coupled to a radiation source and a detector at a proximal end thereof, transmitting source electromagnetic radiation from the radiation source to a distal end of the at least one optical fiber, measuring an intensity of backscattered electromagnetic radiation, determining a ratio of an intensity of backscattered electromagnetic radiation of at least a first wavelength to an intensity of backscattered electromagnetic radiation of at least a second wavelength, and determining a location of a distal tip of the catheter based on a value of the ratio.

In yet additional embodiments, a method of determining one or more properties of a catheter in a patient comprises advancing a catheter in vasculature of a patient, the catheter coupled to at least one radiation source and at least one detector, transmitting source electromagnetic radiation from the at least one radiation source out of the catheter proximate a distal tip thereof, measuring an intensity of backscattered electromagnetic radiation from the at least one radiation source with the at least one detector, and providing a signal indicative of a location of the distal tip within the vasculature based, at least in part, on the measured intensity of the backscattered electromagnetic radiation. In some embodiments, the signal indicative of the location of the distal tip within the vasculature is based on the measured intensity of the backscattered electromagnetic radiation.

In other embodiments, a system for determining one or more properties of a catheter within a patient comprises at least one radiation source coupled to a catheter and configured to transmit source electromagnetic radiation out of the catheter proximate a distal tip thereof, at least one detector operably coupled to the catheter and configured to measure an intensity of backscattered electromagnetic radiation from the at least one radiation source received at a location proximate the distal tip of the catheter, and a computing system configured to provide a signal indicative of a location of the distal tip of the catheter based, at least in part, on a measured intensity of the backscattered electromagnetic radiation. In some embodiments, the signal indicative of the location of the distal tip within the vasculature is based on the measured intensity of the backscattered electromagnetic radiation.

In further embodiments, a method of determining one or more properties of a catheter in a patient comprises advancing a catheter in vasculature of a patient, the catheter coupled to at least one radiation source and at least one detector, transmitting source electromagnetic radiation from the at least one radiation source to and out of a distal tip of the catheter, measuring an intensity of backscattered electromagnetic radiation from the at least one radiation source with the at least one detector, and at least one of determining at least one property of the catheter based, at least in part, on the measured intensity of the backscattered electromagnetic radiation, and visually displaying the measured intensity of the backscattered electromagnetic radiation. In some embodiments, the signal indicative of the location of the distal tip within the vasculature is based on the measured intensity of the backscattered electromagnetic radiation.

In additional embodiments, a method of determining one or more properties of a catheter in a patient comprises receiving, at a processor operably coupled to the catheter, an indication of an intensity of source electromagnetic radiation transmitted from an emitter from a location proximate a distal tip of a catheter within vasculature of a patient, receiving, at the processor, an indication of an intensity of backscattered electromagnetic radiation proximate the distal tip as measured by a receiver, and providing a signal indicative of a location of the distal tip of the catheter based at least in part on, and in some forms based on, a measured intensity of the backscattered electromagnetic radiation.

In yet additional embodiments, a system comprises a computing system configured to be operably coupled to each of a radiation source and a detector, the computing system comprising a memory configured to store data related to an intensity of source electromagnetic radiation transmitted from the radiation source and emitted from a distal tip of a catheter, and a processor configured to receive an indication of an intensity of backscattered electromagnetic radiation measured by the detector and provide a signal indicative of a location of the distal tip of the catheter based at least in part on, and in some forms based on, the measured intensity of the backscattered electromagnetic radiation. The system further comprises a user interface configured to provide at least one of an audible and a visual indication of the location of the distal tip of the catheter.

DETAILED DESCRIPTION

Figure 1:
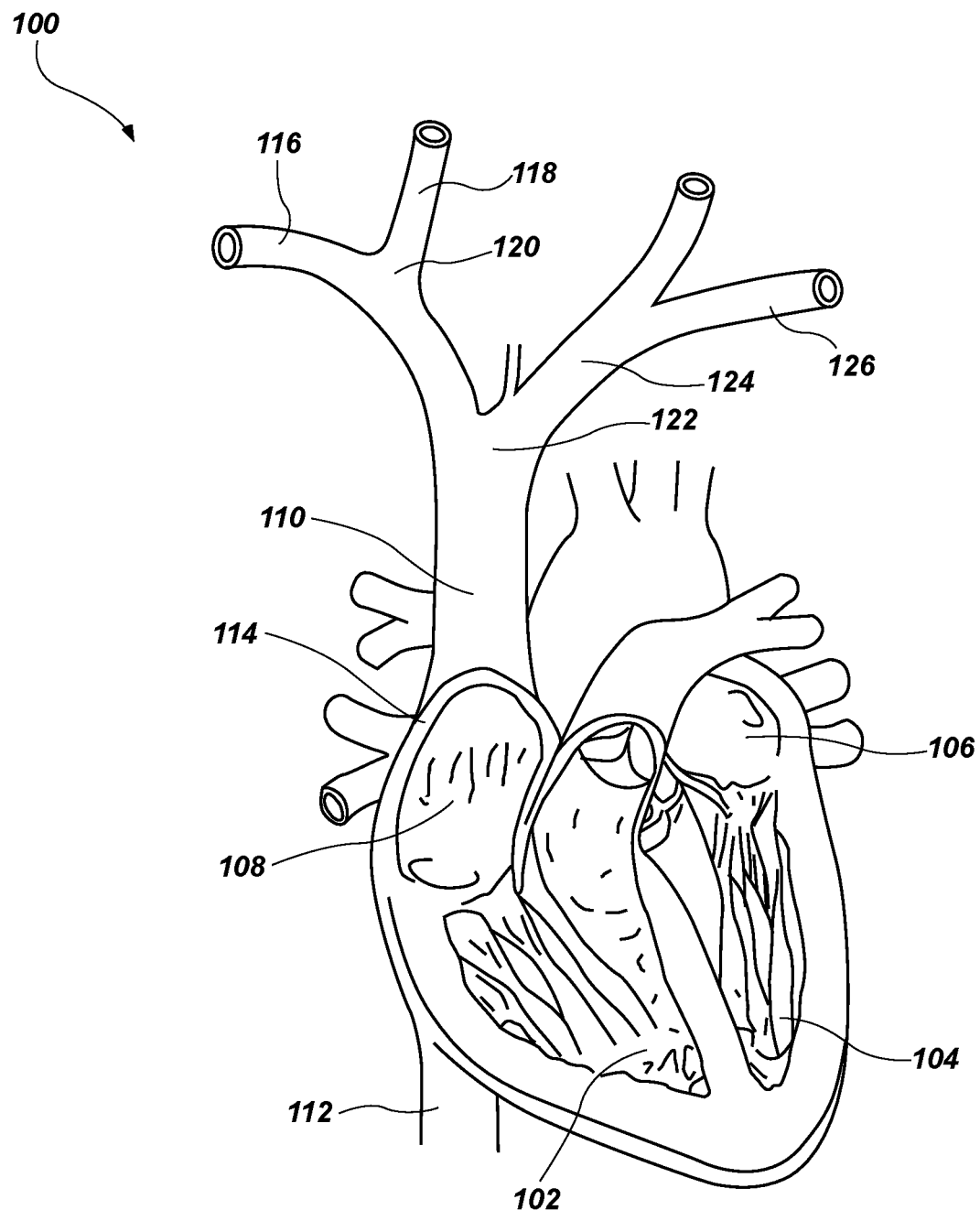
FIG. 1 is a simplified schematic illustrating a human heart and related anatomy.

Illustrations presented herein are not meant to be actual views of any particular material, component, or system, but are merely idealized representations that are employed to describe embodiments of the disclosure.

The following description provides specific details, such as material types, compositions, material thicknesses, and operating conditions in order to provide a thorough description of embodiments of the disclosure. However, a person of ordinary skill in the art will understand that the embodiments of the disclosure may be practiced without employing these specific details. Indeed, the embodiments of the disclosure may be practiced in conjunction with conventional techniques employed in the industry. In addition, the description provided below does not form a complete process flow for placing a peripherally inserted central catheter (PICC), central venous catheter, or any other type of catheter in a patient or for forming related tip confirmation systems. Further, the description provided below does not form a complete process flow for tracking a distal tip of the catheter during advancement thereof in a patient, for determining a diameter or cross-sectional area of the vasculature proximate the distal tip, or for determining a location of the distal tip of the catheter relative to the cavoatrial junction. Only those process acts and structures necessary to understand the embodiments of the disclosure are described in detail below. A person of ordinary skill in the art will understand that some components (e.g., valves, clamps, medicaments, tubing, fiber optic cables, optical connectors, electromagnetic radiation sources, detectors, and the like) are inherently disclosed herein and that adding various conventional process components and acts would be in accord with the disclosure. Additional acts or materials to determine a location of a catheter or one or more other properties of a catheter within a patient may be performed by conventional techniques.

As used herein, the term "catheter" means and includes an elongated, tubular element that is configured to be inserted into a body of a patient such as through the patient's vasculature (e.g., into the patient's veins or arteries), and may include, by way of nonlimiting example, a central venous catheter (CVC), a peripherally inserted central catheter, a jugular venous catheter for internal jugular vein (IJV) catheterization, or other types of catheters. Catheters, as described herein, may be used for any type of central venous access.

The systems and methods described herein may offer advantages compared to conventional tip confirmation systems and methods of determining a location of a distal tip of a catheter. For example, according to the methods described herein, one or more properties of a catheter, such as a location of the distal tip thereof, a direction of advancement thereof relative to blood flow, a size of vasculature proximate the distal tip, whether the distal tip has passed a junction in the vasculature, or combinations thereof, may be determined without use of an electrocardiogram (ECG). Accordingly, the systems and methods may be suitable for patients with implanted electronic devices (IEDs) (e.g., a pacemaker), patients with an arrhythmia, or with one or more other conditions for which ECGs pose a substantial risk. In addition, because of the relatively smaller size of the systems described herein, the systems and methods may be suitable for use in pediatric patients to a much greater extent than conventional tip confirmation systems. Further, the systems and methods described herein may facilitate placement of the catheter without use of a surrogate marker, such as, for example, one or more electrodes placed on an external surface of a patient during placement of the catheter.

According to embodiments disclosed herein, a method of determining a location of a distal tip of a catheter during advancement and placement thereof within the vasculature of a patient includes providing a catheter including an electromagnetic radiation source (e.g., at least one fiber optic cable, a light-emitting diode, one or more lasers, etc.) therein. For example, at least one fiber optic cable may extend through the catheter and may be positioned and configured to transmit electromagnetic radiation to a location proximate the distal tip of the catheter. A distal end of the at least one fiber optic cable may be disposed coincident with the distal tip of the catheter, slightly proximal of the distal tip, or slightly distal of the distal tip. Electromagnetic radiation may be transmitted from a radiation source through at least one optical fiber of the fiber optic cable to the blood proximate the distal tip, to the tissue proximate the distal tip, or to both. A portion of the electromagnetic radiation may be backscattered or otherwise reflected by the blood, the vasculature, or the tissue proximate the distal tip and may be detected by a detector coupled to the catheter (e.g., such as to the at least one optical fiber or at least another optical fiber of the fiber optic cable). The location of the distal tip of the catheter in relation to the cavoatrial junction may be determined based on the intensity of the electromagnetic radiation provided by the radiation source relative to the intensity of the backscattered electromagnetic radiation detected by the detector. In some embodiments, when the intensity of the electromagnetic radiation from the source relative to the intensity of the backscattered electromagnetic radiation changes by a predetermined amount (e.g., is less than or greater than a predetermined value), advancement of the catheter may be stopped responsive to determining that the distal tip is in or proximate the cavoatrial junction. In some embodiments, a diameter, or a distance from the distal tip of the catheter to a wall of the vasculature (e.g., a vein, an artery, etc.) proximate the distal tip may be determined based on the intensity of the electromagnetic radiation from the source relative to the intensity of the backscattered electromagnetic radiation at one or more wavelengths (e.g., at one wavelength, at two wavelengths, or across a spectrum). In other embodiments, the location of the distal tip of the catheter relative to the cavoatrial junction may be determined based on the intensity of backscattered electromagnetic radiation having at least a first wavelength relative to an intensity of backscattered electromagnetic radiation having at least a second wavelength. In additional embodiments, a direction of advancement of the distal tip may be determined based on one or more of an intensity or a wavelength of the backscattered electromagnetic radiation, which may facilitate determination by the clinician that the catheter is being advanced properly and has not, for example, deviated from an intended pathway to the CAJ.

As used herein, the term "diameter" means and includes a dimension of a cross-sectional arcuate shape, such as a circle, an ellipse, an oval, an oblong shape, or any other shape including at least one curved surface and may be used to refer to structures having differently shaped cross-sections. A diameter of a structure may refer to a selected distance between substantially opposing walls of the structure, the substantially opposing walls being separated by about 180°.

As used herein, the term "vasculature" means and includes veins, arteries, vessels, organs, or other components of the vascular or blood circulatory system.

As used herein, the terms "backscattered electromagnetic radiation" and "reflected electromagnetic radiation" may be used to refer to electromagnetic radiation that returns to a location proximate a source of the electromagnetic radiation and which may be received and measured by a detector.

FIG. 1 is a simplified schematic of a heart 100 and related anatomy. The heart 100 may include, among other things, a right ventricle 102, a left ventricle 104, a left atrium 106, and a right atrium 108. Deoxygenated blood that has circulated through the body enters the right atrium 108 of the heart 100 through a superior vena cava (SVC) 110 and an inferior vena cava 112. A cavoatrial junction (CAJ) 114 may be defined as a location where the superior vena cava 110 meets a superior wall of the right atrium 108. A cross-sectional area of the superior vena cava 110 may be larger than a cross-sectional area of the veins that lead up to the superior vena cava 110. In addition, a color (and, therefore, a reflectance spectrum, a reflectance at one or more wavelengths, or both) of tissue in the vasculature leading to the superior vena cava 110 may be different than a color (and, therefore, a reflectance spectrum, a reflectance at one or more wavelengths, or both) of tissue in the cavoatrial junction 114. In general, when a PICC is placed within a patient, it is desired to place the distal tip of the PICC at the cavoatrial junction 114 proximate the superior vena cava 110. In an adult human being, the distal tip of the PICC is desirably placed no more than about 5 mm or about 10 mm from the cavoatrial junction 114 in a direction toward the superior vena cava 110. In infants and children, the acceptable distance range is much smaller. According to embodiments described herein, systems and methods for accurately placing a catheter, such as a PICC, proximate the cavoatrial junction 114 are described.

With continued reference to FIG. 1, during placement of a catheter in a patient, the catheter may be advanced in the patient through, for example, the patient's arm to a first vein 116 and ultimately to the cavoatrial junction 114. Between an insertion point (e.g., the patient's arm) and the cavoatrial junction 114, the vasculature may include one or more junctions at which the distal tip of the catheter may deviate from the intended path. For example, at a first junction 120 between the first vein 116 and a second vein 118, the catheter may undesirably advance up the second vein 118. Similarly, at a second junction 122 (e.g., the innominate junction) the catheter may undesirably advance up a third vein 124 (e.g., the brachiocephalic vein (also referred to as the "innominate vein")) toward, for example, the contralateral subclavian vein 126. According to embodiments described herein, a system may be configured to determine when the catheter deviates from the intended course.

Figure 2A:
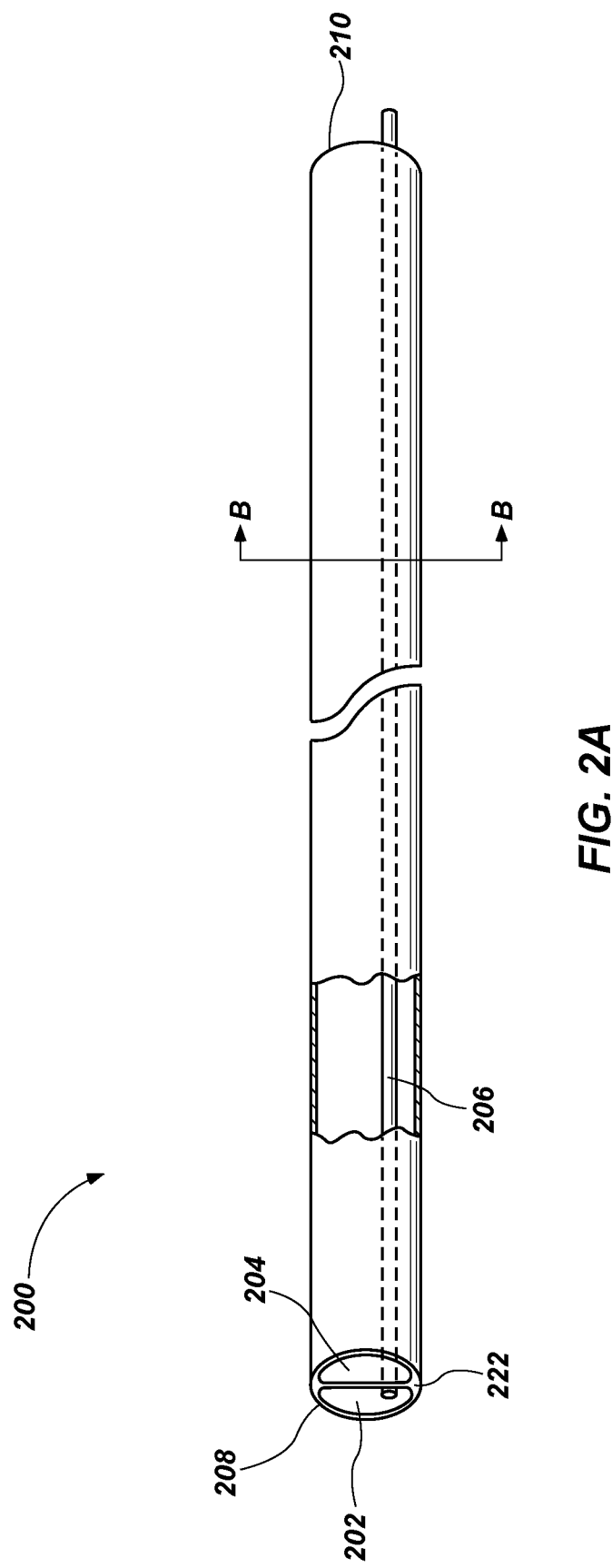
FIG. 2A is a simplified schematic of a catheter including a fiber optic cable extending therethrough, according to an embodiment of the disclosure.

FIG. 2A illustrates a simplified schematic of a multi-lumen catheter 200, according to an embodiment of the disclosure. The catheter 200 may be configured to be inserted into a patient's vasculature, such as through a patient's arm, until a distal tip 210 thereof is located proximate the patient's cavoatrial junction 114 (FIG. 1). The catheter 200 may have a length between about twelve inches (about 30.48 cm) and about forty-eight inches (about 121.92 cm), such as between about twelve inches (about 30.48 cm) and about twenty-four inches (about 60.96 cm), between about twenty-four inches (about 60.6 cm) and about thirty-six inches (about 91.44 cm), or between about thirty-six inches (91.44 cm) and about forty-eight inches (about 121.92 cm). However, the disclosure is not so limited and the catheter 200 may have a different length than those described above.

The catheter 200 may include at least a first lumen 202 and at least a second lumen 204 separated from the first lumen by a wall 222. The first lumen 202 may be sized and configured to receive a fiber optic cable 206 along an interior thereof. The fiber optic cable 206 may extend from a proximal end 208 to the distal tip 210 of the catheter 200. In some embodiments, a distal end of the fiber optic cable 206 may be disposed at or proximate to the distal tip 210 of the catheter 200. The distal end of the fiber optic cable 206 may be located between about 0 mm and about 3 mm away from the distal tip 210 of the catheter 200, such as between about 0 mm and about 1 mm, between about 1 mm and about 2 mm, or between about 2 mm and about 3 mm from the distal tip 210. The distal end of the fiber optic cable 206 may be between about 0 mm and about 3 mm from the distal tip 210 in a direction toward the proximal end 208 or between about 0 mm and about 3 mm from the distal tip 210 in a direction away from the proximal end 208. In some embodiments, the distal end of the fiber optic cable 206 may be between about 2 mm and about 3 mm from the distal tip 210 in a direction away from the proximal end 208. A proximal end of the fiber optic cable 206 may be located outside the patient and may be configured to be coupled to one or more components configured to provide and detect electromagnetic energy. The second lumen 204 may be sized and configured to receive and transport medicaments to the patient. Although the catheter 200 of FIG. 2A is a dual lumen catheter, the catheter 200 may include any number of lumens (e.g., one, three, four, etc.). As will be described herein with reference to FIG. 2I, the catheter 200 may comprise a single lumen catheter.

The fiber optic cable 206 may be configured to transmit electromagnetic energy from a source, such as at a location outside the vasculature to the distal tip 210 of the catheter 200. The fiber optic cable 206 may further be configured to transmit electromagnetic radiation that is backscattered by the blood, by vascular walls, or by tissue in the vasculature (e.g., tissue in the cavoatrial junction), or a combination thereof so that at least one property of the backscattered electromagnetic radiation may be measured.

Figure 2B:
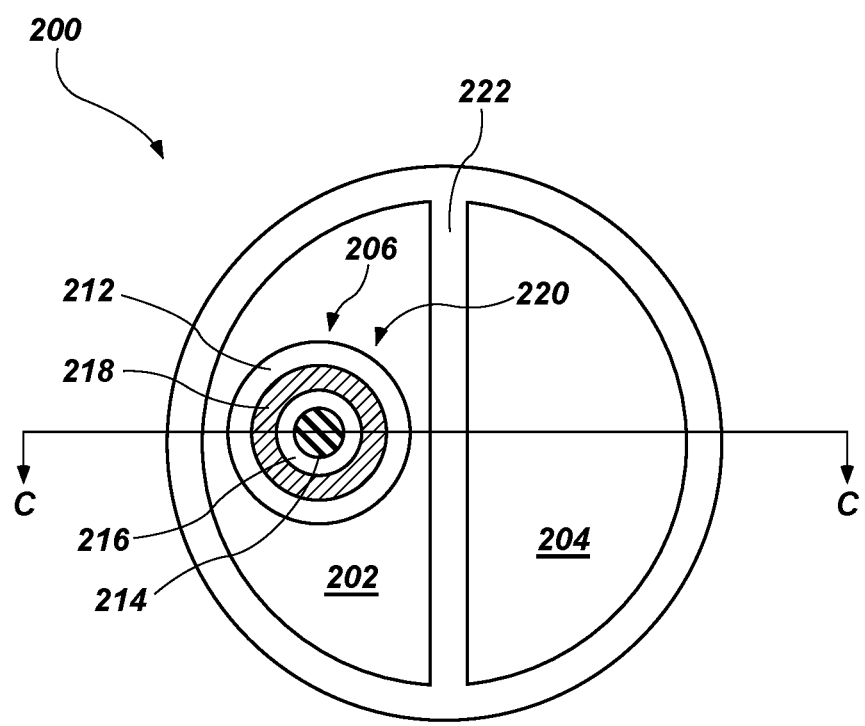
FIG. 2B is a simplified transverse cross-sectional view of the catheter of FIG. 2A, taken along section line B-B of FIG. 2A.

FIG. 2B illustrates a cross-sectional view of the catheter 200 taken along section line B-B in FIG. 2A, wherein the fiber optic cable 206 is disposed in the first lumen 202. The fiber optic cable 206 may comprise a single-fiber cable including, for example, a sheath 212 surrounding an optical fiber assembly 220 which may include a core optical fiber 214 surrounded by cladding 216. The cladding 216 may be surrounded by a buffer layer 218 or a jacket material. The cable diameter may be on the order of about 300 μm for a multimode fiber cable, and smaller for a single mode fiber cable.

The optical fiber assembly 220 may be configured to receive source electromagnetic radiation from a radiation source and transmit the source electromagnetic radiation to a distal end of the optical fiber assembly 220. In some embodiments, the optical fiber assembly 220 may comprise one or more single mode or multi-mode optical fibers. The optical fiber assembly 220 may also be configured to receive and detect electromagnetic radiation that is backscattered by one or more of the blood, the vascular walls, or tissue located in and/or proximate to the vasculature and transmit the backscattered electromagnetic radiation to a detector configured to measure at least one property (e.g., an intensity) of the backscattered electromagnetic radiation. In some embodiments, the optical fiber assembly 220 may be configured to measure a spectrum of the backscattered electromagnetic radiation.

Figure 2C:
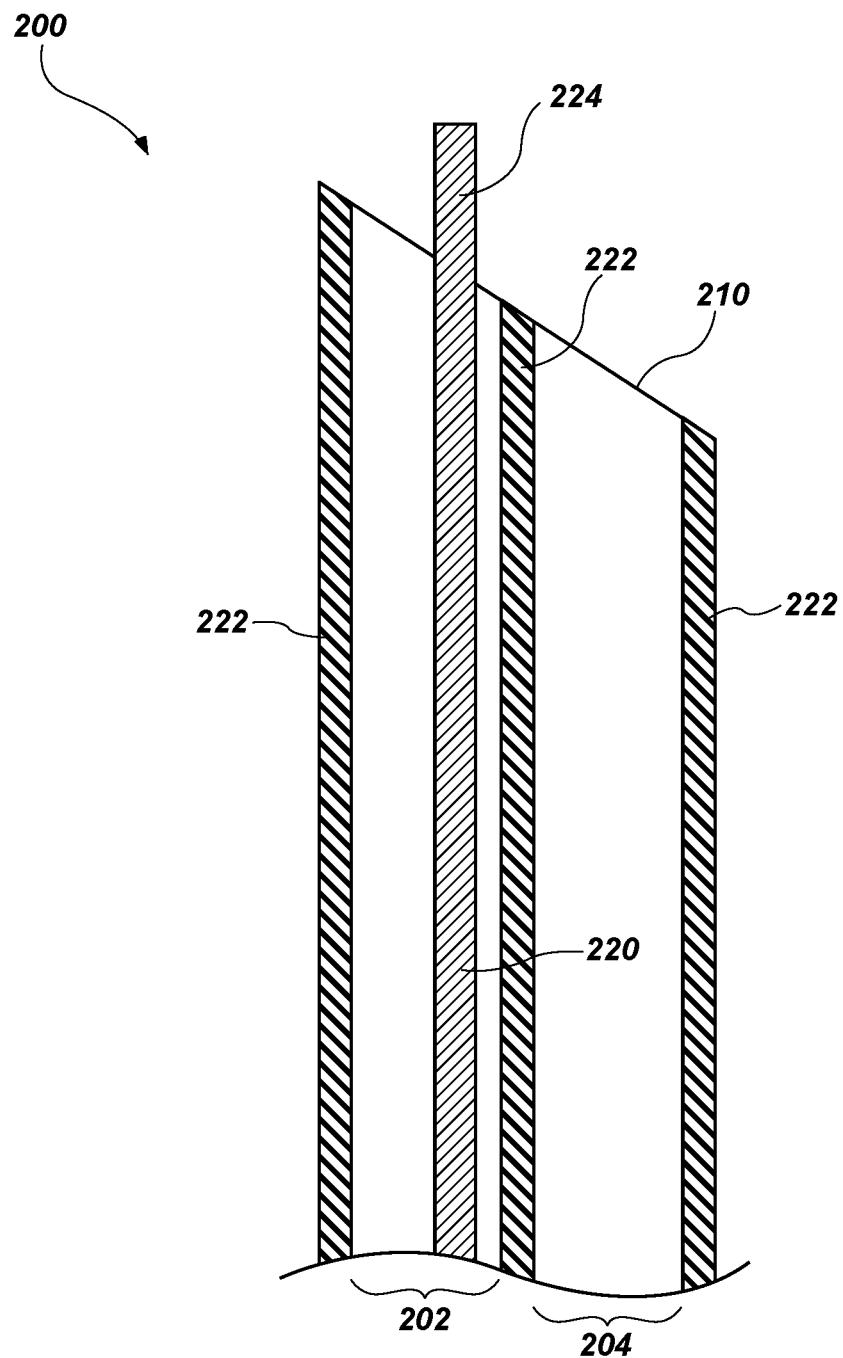
FIG. 2C is a simplified longitudinal cross-sectional view of the catheter of FIG. 2A, taken along section line C-C of FIG. 2B.

FIG. 2C is a cross-sectional view of the catheter 200 taken along a longitudinal axis thereof, illustrating the optical fiber assembly 220 disposed in the first lumen 202. As illustrated, the optical fiber assembly 220, and hence, the core optical fiber 214 may include a substantially planar, smooth, and optionally polished end surface in a plane that is substantially orthogonal to a longitudinal axis of the optical fiber assembly 220. Stated another way, the core optical fiber 214 may be cleaved at a distal end 224 thereof at an angle of about 90° from the longitudinal axis of the core optical fiber 214. However, the disclosure is not so limited and the core optical fiber 214 may be shaped differently at the distal end 224.

Figure 2D:
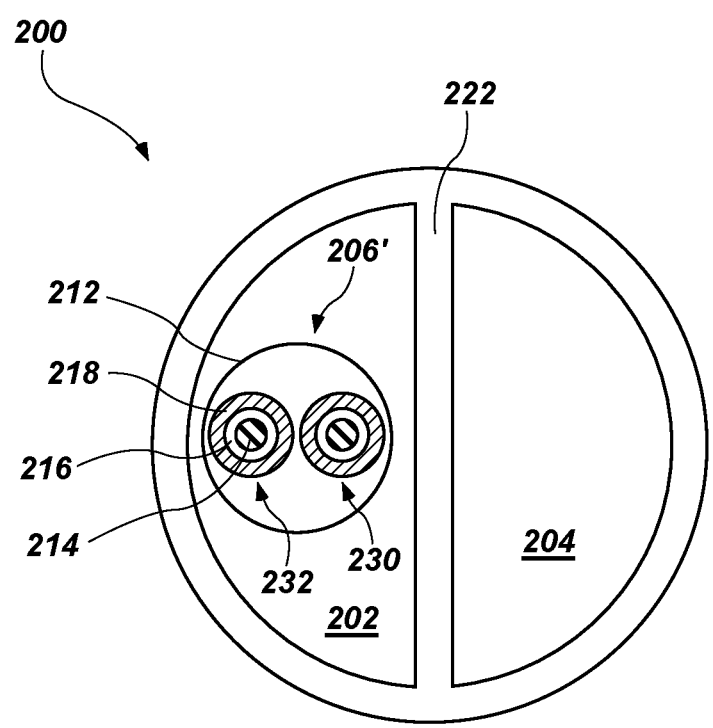
FIG. 2D is a simplified transverse cross-sectional view of a catheter according to another embodiment of the disclosure.

Although FIG. 2B and FIG. 2C illustrate only one optical fiber assembly 220, it is contemplated that in other embodiments, the fiber optic cable 206 may include more than one optical fiber assembly 220. By way of nonlimiting example and as illustrated in FIG. 2D, a fiber optic cable 206' may comprise a source optical fiber assembly 230 and a detector optical fiber assembly 232, each including a core optical fiber 214 surrounded by cladding 216 and the buffer layer 218. In some such embodiments, the sheath 212 may surround the source optical fiber assembly 230 and the detector optical fiber assembly 232. In some embodiments, a distal end of the core optical fibers 214 of the source optical fiber assembly 230 and the detector optical fiber assembly 232 may be longitudinally offset from each other. In some such embodiments, at least one of the source optical fiber assembly 230 and the detector optical fiber assembly 232 may be longitudinally offset from the other of the source optical fiber assembly 230 and the detector optical fiber assembly 232. For example, a distal end of the detector optical fiber assembly 232 may be located closer to the distal tip 210 of the catheter 200 than a distal end of the source optical fiber assembly 230. In other embodiments a distal end may of the source optical fiber assembly 230 may be located closer to the distal tip 210 of the catheter 200 than a distal end of the detector optical fiber assembly 232. In some embodiments, a longitudinal distance between the distal ends of the source optical fiber assembly 230 and the detector optical fiber assembly 232 is between about 1 mm and about 5 mm, such as between about 3 mm and about 5 mm, such as about 4 mm or about 3 mm.

Figure 2E:
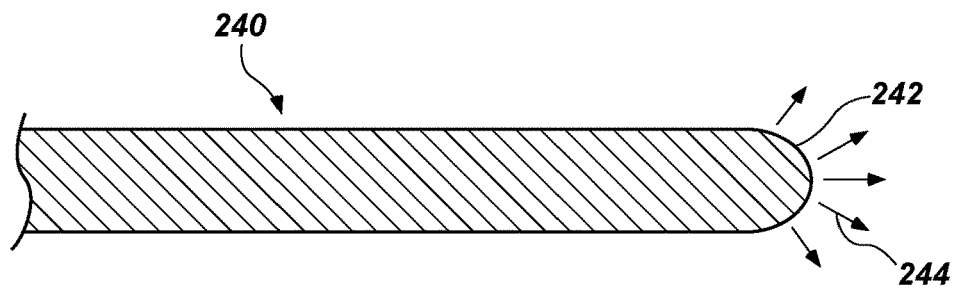
FIG. 2E through FIG. 2H are simplified longitudinal cross-sectional views of an optical fiber, according to various embodiments of the disclosure.

FIG. 2E through FIG. 2H are longitudinal cross-sectional views of optical fibers having different distal end configurations. The core optical fiber 214 (FIG. 2B, FIG. 2D) may comprise one or more of the optical fibers illustrated in FIG. 2E through FIG. 2H. FIG. 2E is an optical fiber 240 that may include a distal end 242 having a hemispherical or elliptical shape. In some embodiments, the optical fiber 240 may be configured to transmit electromagnetic radiation in a plurality of directions from the distal end 242, as indicated by arrows 244. The optical fiber 240 may similarly be configured to receive backscattered electromagnetic radiation incident upon the distal end 242 from a plurality of directions.

Figure 2F:
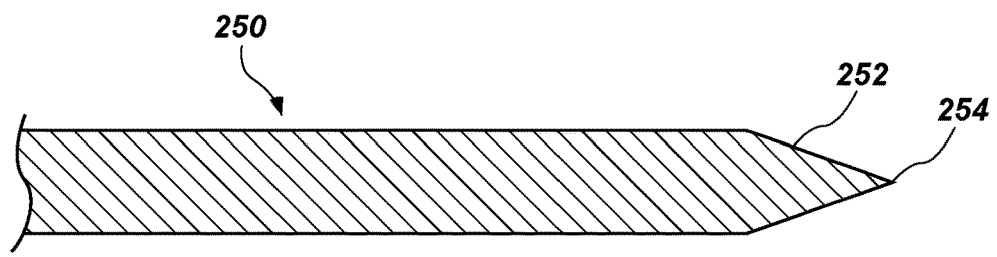
Figure 2G:
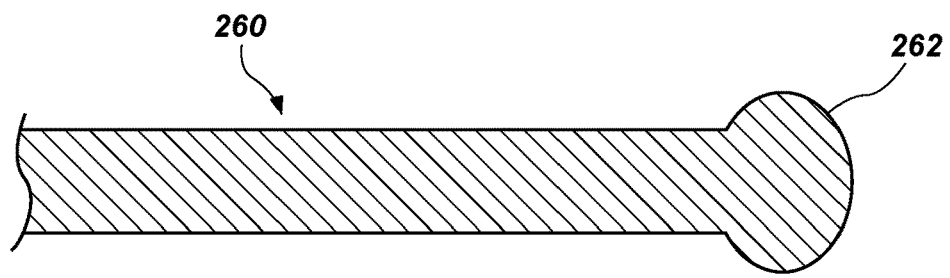

FIG. 2F illustrates another optical fiber 250 according to embodiments of the disclosure. The optical fiber 250 may include a conical-shaped distal end 252. The conical-shaped distal end 252 may, in some embodiments, converge to a point 254. FIG. 2G illustrates yet another embodiment of an optical fiber 260. The optical fiber 260 may include a ball-tipped distal end 262 in the form of a so-called "glow ball" shaped and configured to transmit and receive electromagnetic radiation from a plurality of directions.

Figure 2H:
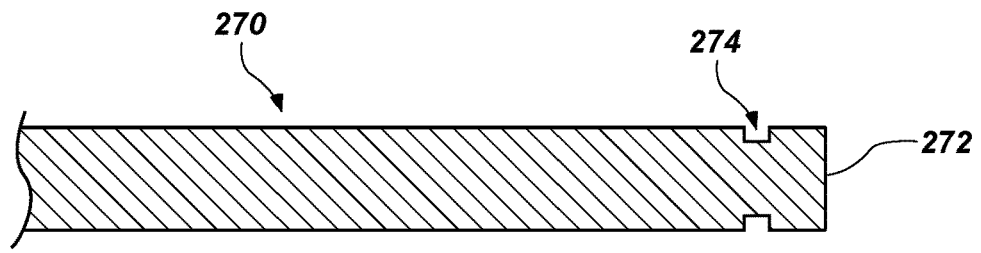

With reference to FIG. 2H, yet another embodiment of an optical fiber 270 is illustrated. The optical fiber 270 may comprise what is referred to in the art as a "side-fire" optical fiber, wherein the optical fiber 270 is configured to transmit and/or receive electromagnetic radiation from a radial location of the optical fiber 270 as opposed to from a distal end 272 thereof, an outer jacket of the optical fiber being removed circumferentially about the optical fiber 270 for radiation emission and receipt. In some embodiments, the distal end 272 may be coated with a reflective coating such that substantially all of the electromagnetic radiation emitted from or received by the optical fiber 270 is emitted from or received at side portions 274 of the optical fiber 270. In some embodiments, such as that of FIG. 2H, the optical fiber 270 may be shaped and configured for determining a diameter of the vasculature of a patient.

Although FIG. 2E through FIG. 2H illustrate optical fibers having distal ends having various configurations, the disclosure is not so limited. For example, the optical fibers used herein may include any type of optical fiber having any suitable configuration of distal end(s) and the disclosure is not limited to the specific optical fibers described above.

Figure 2I:
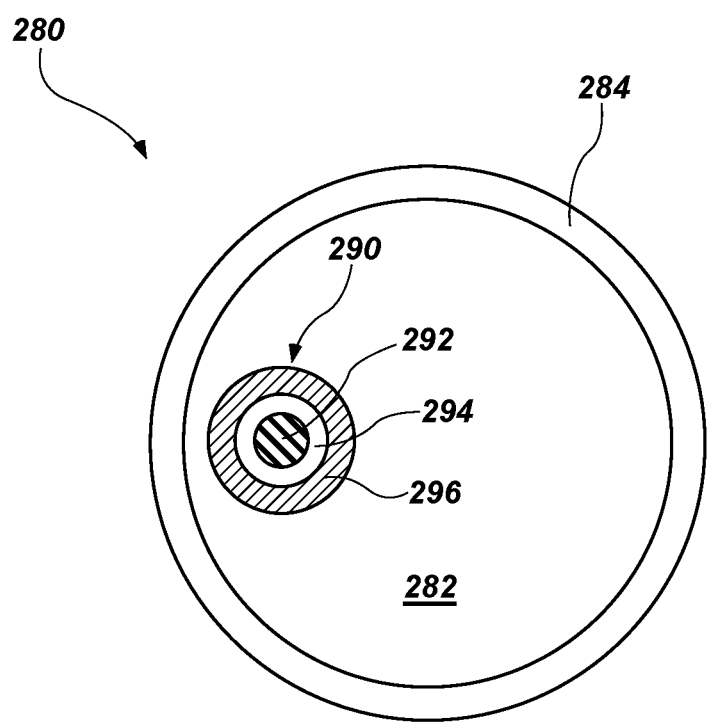
FIG. 2I is a simplified transverse cross-sectional view of a catheter, according to another embodiment of the disclosure.

Although the catheter 200 has been described as comprising a multi-lumen catheter, it is contemplated that in other embodiments, the catheter comprises a single-lumen catheter. FIG. 2I is a simplified transverse cross-sectional view of a catheter 280. The catheter 280 may include a lumen 282 defined by a wall 284 of the catheter 280. A fiber optic cable 290 comprising a single core optical fiber 292 may be disposed within the lumen 282. The fiber optic cable 290 may comprise, for example, a cladding 294 surrounding the core optical fiber 292 and a buffer layer 296 surrounding the cladding 294.

In some embodiments, the fiber optic cable 290 may have an outer diameter of about 125 µm. In embodiments employing a single mode fiber optic cable comprising a single fiber, the fiber optic cable may have an outer diameter of about 50 µm. In some such embodiments, the fiber optic cable 290 may be disposed in a catheter sized and configured for placement within a pediatric patient. In some such embodiments, the catheter 280 may comprise, for example, a 1.9 French single lumen catheter (i.e., 23 gauge) with an inner diameter of about 300 µm and an outer diameter of about 633 µm.

Figure 3:
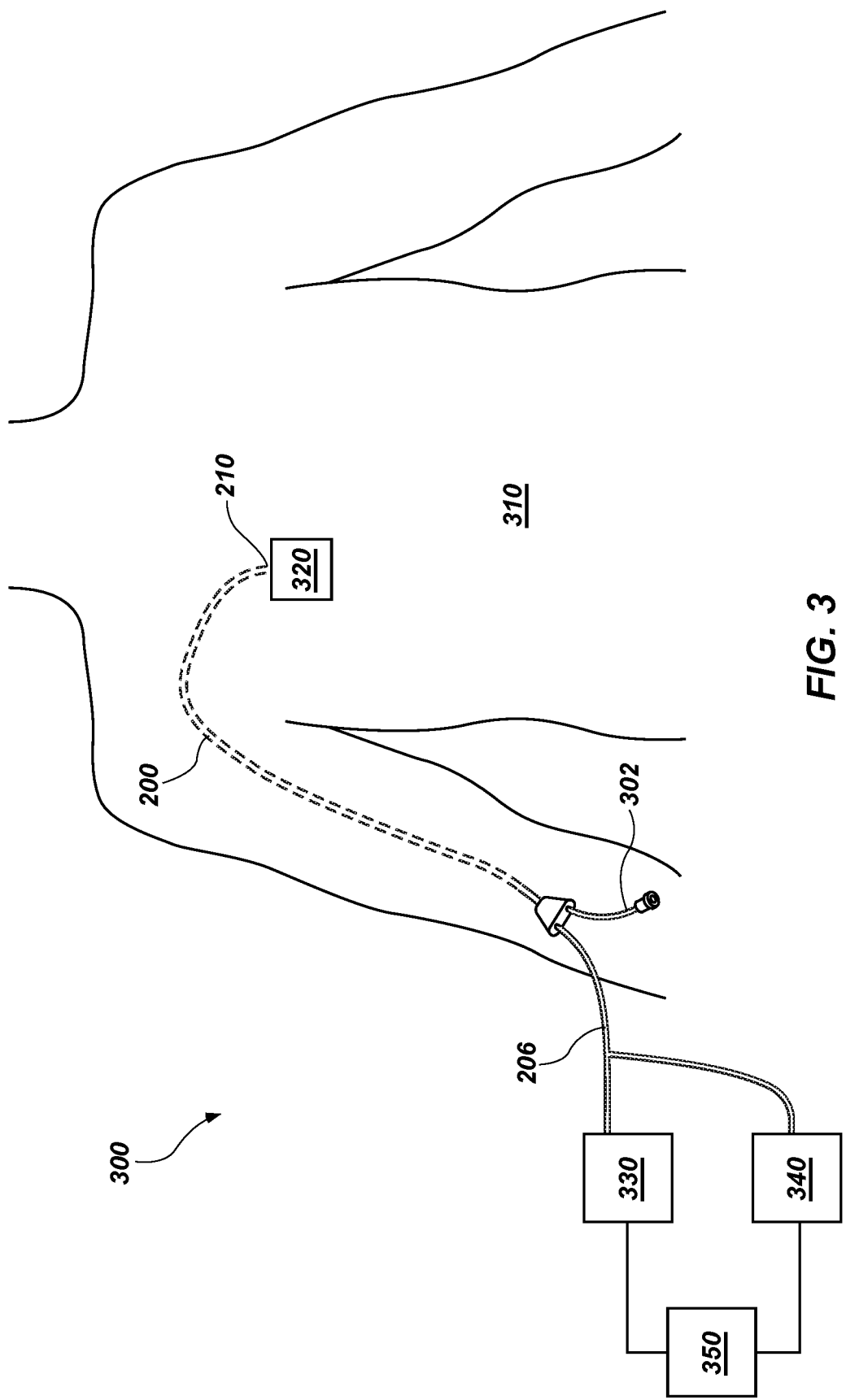
FIG. 3 is a simplified schematic of a system configured for determining a location of a catheter relative to the cavoatrial junction, according to an embodiment of the disclosure.

FIG. 3 is a simplified schematic illustrating a system 300 (e.g., a tip confirmation system) for determining a location of the distal tip 210 of the catheter 200 during insertion of the catheter 200 into the vasculature (e.g., a vein, an artery, etc.) of patient a 310. During insertion of the catheter 200, it may be desired to place the distal tip 210 proximate the cavoatrial junction 114 (FIG. 1). The system 300 may be used for determining one or more properties of the catheter 200, such as a location of a distal tip 210 relative to a heart 320 of the patient 310 and, more particularly, relative to the cavoatrial junction 114. In some embodiments, the system 300 may be used for determining a diameter of the vasculature of the patient during insertion of the catheter 200 and may also be used to create a map of a diameter of the patient's vasculature as the catheter 200 is inserted. In some embodiments, a distance from the distal tip 210 to a surrounding wall of the patient's vasculature may be determined with the system 300. In additional embodiments, the system 300 may be configured to determine whether the distal tip 210 is being advanced in the proper direction or may be configured to track a location of the distal tip 210 in the vasculature of the patient, such as, for example, whether the distal tip 210 has passed one or more of the first junction 120 (FIG. 1) or the second junction 122 (FIG. 1).

The catheter 200 may extend within the vasculature of the patient 310, such as from the patient's arm to a location proximate the heart 320. In some embodiments, the catheter 200 may comprise a multi-lumen catheter, such as a dual lumen catheter, as described above with reference to FIG. 2A through FIG. 2D. At least one lumen of the catheter 200 may be configured to receive medicaments, such as through a medicament deliver tube 302. At least another lumen of the catheter 200 may include at least a fiber optic cable 206 disposed therein, as described above with reference to FIG. 2A through FIG. 2D. In other embodiments, the catheter 200 comprises a single lumen catheter, wherein the fiber optic cable is disposed in the lumen and withdrawn from the lumen after placement of the catheter 200 in the patient, as described above with reference to FIG. 2I.

A portion of the fiber optic cable 206 may be located outside the patient 310 after insertion. One or more optical connectors may couple optical fibers of the fiber optic cable 206 to a radiation source 330 and a detector 340, each located outside the patient 310. For example, an optical connector may couple the fiber optic cable 206 to the radiation source 330, which may be configured to provide source electromagnetic radiation to at least one optical fiber and to the detector 340, which may be configured to measure backscattered electromagnetic radiation that is reflected by the blood, the vasculature, tissue in or of the vasculature, or combinations thereof, proximate the distal tip 210 of the catheter 200. In some embodiments, the radiation source 330 and the detector 340 are coupled to a fiber optical fiber assembly 220 (FIG. 2A, FIG. 2I) comprising a single optical fiber. In other embodiments, the radiation source 330 is operably coupled to a source optical fiber assembly 230 (FIG. 2D) and the detector 340 is operably coupled to a detector optical fiber assembly 232 (FIG. 2D).

The radiation source 330 and the detector 340 may be operably coupled to a computing system 350 configured to aid a user (e.g., a clinician) in determining one or more properties of the catheter 200, such as a location of the distal tip 210 of the catheter 200 relative to the cavoatrial junction 114 (FIG. 1), whether the catheter 200 is being advanced in the proper direction, and inform the user when to stop advancement of the catheter 200 in the patient 310.

The radiation source 330 may be configured to provide source electromagnetic radiation to a distal tip 210 of the catheter 200, such as through at least one optical fiber of the fiber optic cable 206 coupled thereto. In some embodiments, the radiation source 330 may be configured to provide source electromagnetic radiation having a substantially monochromatic (e.g., substantially fixed and uniform) wavelength at one or more wavelengths (e.g., at two or more wavelengths). In some embodiments, the radiation source 330 may be configured to provide source electromagnetic radiation wherein at least about 90 percent of the source electromagnetic radiation has a wavelength that falls within a range of about 10 nm. In some embodiments, the substantially monochromatic wavelength source radiation, or other source radiation, may be provided by a commercially available laser. The substantially monochromatic wavelength may be any suitable wavelength in the electromagnetic spectrum. By way of nonlimiting example, the one or more substantially monochromatic wavelengths may have a wavelength of about 800 nm, about 635 nm, about 633 nm, about 628 nm, about 612 nm, about 594 nm, about 578 nm, about 543 nm, about 532 nm, about 523 nm, about 511 nm, or another wavelength. In some embodiments, the wavelength employed is within the infrared or near-infrared region of electromagnetic region. The electromagnetic radiation may have a wavelength ranging from the visible spectrum (e.g., such as within the red region) to the near-infrared region of electromagnetic radiation, such between about 450 nm and about 1,100 nm, between about 685 nm and about 750 nm, or between about 750 nm and about 1,100 nm. In some embodiments, the radiation source 330 is configured to provide the source electromagnetic radiation at a first substantially monochromatic wavelength between about 450 nm and about 650 nm and at least a second substantially monochromatic wavelength between about 750 nm and about 950 nm.

In some embodiments, the radiation source 330 comprises a laser, such as a near-infrared (NIR) laser. The laser may comprise a solid-state laser, a diode-pumped laser, or a gas laser, by way of nonlimiting example. Although the radiation source 330 has been described as being configured to provide monochromatic electromagnetic radiation at one or more wavelengths, it is contemplated that in other embodiments, the radiation source 330 may be configured to provide broadband electromagnetic radiation configured to provide the source electromagnetic radiation over a range of wavelengths. In yet other embodiments, the radiation source 330 may be configured to provide monochromatic electromagnetic radiation having different wavelengths than those described above. In some embodiments, the radiation source 330 comprises a light-emitting diode (LED) configured to emit, for example, monochromatic electromagnetic radiation having a wavelength between about 450 nm and about 1,100 nm.

The radiation source 330 may be configured to provide the electromagnetic radiation at a power between about 30 mW and about 70 mW, such as between about 30 mW and about 50 mW or between about 50 mW and about 70 mW.

In some embodiments, the radiation source 330 is configured to provide polarized electromagnetic radiation and includes a polarizer (i.e., filter) configured to only pass light of a specific polarization therethrough. In other embodiments, the electromagnetic radiation may be unpolarized or only partially polarized.

The radiation source 330 may be configured to provide the electromagnetic radiation at a range of frequencies. The electromagnetic radiation may be provided at a frequency between about 3 KHz and about 50 KHz, such as between about 5 KHz and about 40 KHz, or between about 10 KHz and about 30 KHz. In some embodiments, the electromagnetic radiation may exhibit a frequency of about 20 KHz.

The radiation source 330 may be configured to transmit the electromagnetic radiation to the distal tip 210 of the catheter 200 (e.g., through the optical fiber assembly 220, 230 (FIG. 2B, FIG. 2C, FIG. 2D)) in pulses and in a plurality of different waveforms. The electromagnetic radiation may exhibit a square waveform, a rectangular waveform, a triangular waveform, a sinusoidal waveform, a sawtooth waveform, a pulse waveform, or another type of waveform. In some embodiments, the electromagnetic radiation exhibits a square waveform. In some embodiments, a current (and, therefore, a power) of the radiation source 330 may be modulated. By way of nonlimiting example, the power to the radiation source 330 and, therefore, the source electromagnetic radiation therefrom may be pulsed between at least two different intensities, for example between zero or another baseline intensity and a selected full intensity, employing a 50% duty cycle. It is believed that providing the source electromagnetic radiation from the radiation source 330 in pulses increases a signal to noise ratio of a received or backscattered electromagnetic radiation and facilitates improved detection of the backscattered electromagnetic radiation.

In some embodiments, the system 300 may further include a multiplexer configured to select one of several inputs (e.g., input wavelengths) and alternate between two or more wavelengths provided by the radiation source 330. Accordingly, in some embodiments, the radiation source 330 may be configured to provide, for example, electromagnetic radiation exhibiting at least a first wavelength (e.g., a first substantially monochromatic wavelength) and electromagnetic radiation exhibiting at least a second wavelength (e.g., a second substantially monochromatic wavelength). Of course, it is contemplated that the radiation source 330 may be configured to provide electromagnetic radiation (e.g., substantially monochromatic electromagnetic radiation) at any number of unique wavelengths, or to provide broadband electromagnetic radiation.

During use and operation, the radiation source 330 may provide source electromagnetic radiation to the fiber optic cable 206 (FIG. 2B, FIG. 2C, FIG. 2D) and at least one optical fiber of the fiber optic cable 206 may transmit the source electromagnetic radiation to the distal tip 210 of the catheter 200. In some embodiments, the source electromagnetic radiation is in the near-infrared region of the electromagnetic spectrum. A distal end of at least one optical fiber of the fiber optic cable 206 may be located proximate the distal tip 210 of the catheter 200. By way of nonlimiting example, the distal end of at least one optical fiber of the fiber optic cable 206 may be located between about 0 mm and about 3 mm from distal tip 210 of the catheter 200, such as between about 0 mm and about 1 mm, between about 1 mm and about 2 mm, or between about 2 mm and about 3 mm from the distal tip 210 of the catheter 200. In some embodiments, the distal end of at least one optical fiber of the fiber optic cable 206 may protrude from the distal tip 210 of the catheter 206 a distance between about 2 mm and about 3 mm. Accordingly, the source electromagnetic radiation from the fiber optic cable 206 may be transmitted through the distal tip 210 to one or more of the blood, vascular walls, and tissue located in and/or proximate to the vasculature and other anatomy proximate the distal end of fiber optic cable 206 within the vasculature of the patient 310.

At least a portion of the source electromagnetic radiation transmitted through the fiber optic cable 206 to a location proximate the distal tip 210 of the catheter 200 may be backscattered or otherwise reflected by, for example, one or more of red blood cells, vascular walls, or tissue located in or proximate to the vasculature. The backscattered electromagnetic radiation may be received by at least one optical fiber (e.g., the optical fiber assembly 220) (FIG. 2B, FIG. 2C)) within the fiber optic cable 206. The backscattered electromagnetic radiation may be transmitted through the at least one optical fiber to the detector 340. As described herein, properties of the backscattered electromagnetic radiation may depend, at least in part, on a position of the catheter 200 within the patient. By way of nonlimiting example, an intensity of backscattered electromagnetic radiation at a first wavelength relative to an intensity of backscattered electromagnetic radiation of at least a second wavelength may depend on a location of the distal tip 210 relative to the cavoatrial junction 114 (FIG. 1). As another example, a spectrum of the backscattered electromagnetic radiation may depend on the location of the distal tip 210. In other embodiments, a ratio of an intensity of the source electromagnetic radiation to an intensity of the backscattered electromagnetic radiation may depend, at least in part, on a position of the catheter 200 within the patient. In additional embodiments, a shift in a peak wavelength between electromagnetic radiation from the radiation source 330 and a peak wavelength of the backscattered electromagnetic radiation may correspond to a direction of travel of the distal tip 210 relative to a direction of blood flow. Stated another way, a shift in a wavelength between the electromagnetic radiation from the radiation source 330 and a wavelength of the backscattered electromagnetic radiation may be used to determine a direction of movement of the distal tip 210 relative to the direction of blood flow in the vasculature. In yet other embodiments, an amount (and, therefore, an intensity) of backscattered electromagnetic radiation may be directly proportional to an inner diameter and a cross-sectional area of the vasculature proximate the distal tip 210 of the catheter 200, wherein an intensity of the backscattered electromagnetic radiation increases when the distal tip 210 is located within the vasculature (e.g., a vein, an artery, etc.) having a larger cross-sectional area than when the distal tip 210 is located within vasculature (e.g., a vein, an artery, etc.) having a smaller cross-sectional area. In some embodiments, an intensity of the backscattered electromagnetic radiation may increase during ventricular diastole (i.e., when the ventricles open) and decrease during ventricular systole (i.e., when the ventricles contract). In some embodiments, an intensity of backscattered electromagnetic radiation may be between about 5 and about 6 times larger during ventricular diastole than during ventricular systole. Without wishing to be bound by any particular theory, it is believed that the relative change in intensity of the backscattered electromagnetic radiation during ventricular diastole and ventricular systole is caused by the distal end of the optical fiber contacting the right atrium the during opening of the right ventricle (i.e., during ventricular diastole).

The detector 340 may be configured to measure the backscattered electromagnetic radiation that is transmitted into the blood and the vasculature and reflected from one or more of the blood, the vascular walls, or the tissue proximate the distal end of the catheter 200 through the fiber optic cable 206. By way of nonlimiting example, the detector 340 may be configured to measure backscattered electromagnetic radiation that reflects or backscatters from a volume of red blood cells, such as a volume of red blood cells proximate the distal end of the fiber optic cable 206. The detector 340 may include a photodetector, a spectrometer (which may be used to measure an intensity of a spectrum of backscattered electromagnetic radiation), or a spectrograph, such as an infrared spectrometer, configured to measure at least one property of the backscattered electromagnetic radiation. In some embodiments, the detector 340 is configured to measure one or more of a spectrum of the backscattered electromagnetic radiation, an intensity of the backscattered electromagnetic radiation, and an intensity of the backscattered electromagnetic radiation at one or more wavelengths transmitted through the fiber optic cable 206

(i.e., at one or more wavelengths of the source electromagnetic radiation). In some embodiments, the detector 340 is configured to measure an intensity of backscattered electromagnetic radiation of at least two wavelengths. By way of nonlimiting example, the detector 340 may be configured to measure an intensity of the backscattered electromagnetic radiation at substantially the same wavelength as one or more wavelengths of the source electromagnetic radiation from the radiation source 330. In some embodiments, the detector 340 is configured to measure a wavelength of a peak intensity of the backscattered electromagnetic radiation.

The detector 340 may include a filter array, a grating array, a dichroic mirror, or combinations thereof, each configured to allow radiation of different, selected wavelengths to pass therethrough. In some embodiments, the detector 340 includes a near-infrared spectrometer (such as a near-infrared spectrometer) configured to measure at least one of a spectrum or an intensity of electromagnetic radiation that is transmitted by the fiber optic cable 206. In some embodiments, the detector 340 may be configured to measure an intensity of electromagnetic radiation having substantially the same wavelength as the source electromagnetic radiation from the radiation source 330.

The computing system 350 may be configured to determine a location of the distal tip 210 relative to the cavoatrial junction 114 (FIG. 1). The computing system 350 may be configured to determine a ratio of the intensity of the source electromagnetic radiation to the intensity of the backscattered electromagnetic radiation, a ratio of an intensity of backscattered electromagnetic radiation at a first wavelength (e.g., a first substantially monochromatic wavelength) to an intensity of backscattered electromagnetic radiation at least at a second wavelength (e.g., a second substantially monochromatic wavelength), or a combination thereof. Based on one or both of the ratios, the computing system 350 may be configured to provide an indication of a location of the distal tip 210 of catheter 200 relative to the cavoatrial junction 114. It will be understood, as that term is used herein, that the "ratio" of the intensity of the source electromagnetic radiation to the intensity of the backscattered electromagnetic radiation means and includes a ratio when the intensity of the source electromagnetic radiation is the numerator and the intensity of the backscattered electromagnetic radiation is the denominator as well as the inverse (i.e., when the intensity of the backscattered electromagnetic radiation is the numerator and the intensity of the source electromagnetic radiation is the denominator). Similarly, it will be understood herein that the ratio of the intensity of the backscattered electromagnetic radiation at a first wavelength to the intensity of the backscattered electromagnetic radiation at least at a second wavelength includes values when the intensity of the backscattered electromagnetic radiation at the first wavelength is the numerator and the intensity of the backscattered electromagnetic radiation of at least the second wavelength is the denominator, as well as the inverse values. In other embodiments, the computing system 350 is configured to determine a location of the distal tip 210 relative to the cavoatrial junction 114 (FIG. 1) based on a spectrum of the backscattered electromagnetic radiation. In yet other embodiments, the computing system 350 may be configured to determine a diameter, a cross-sectional area, or both of the vasculature of the patient proximate the distal tip 210 of the catheter 200 based, at least in part, on the intensity of the backscattered radiation or the aforementioned ratio of the intensity of the backscattered electromagnetic radiation at two or more wavelengths. By way of nonlimiting example, a ratio of the intensity of backscattered electromagnetic radiation at a first wavelength (e.g., a wavelength between about 450 nm and about 650 nm, such as about 638 nm) to the intensity of backscattered electromagnetic radiation at a second wavelength (e.g., between about 750 nm and about 950 nm, such as about 833 nm) may change by a predetermined amount (e.g., by at least about 20 percent, at least about 30 percent, at least about 40 percent, etc.), or may fall within a range of predetermined values responsive to advancement of the catheter 200 into the cavoatrial junction. By way of nonlimiting example, the ratio may decrease as the distal tip 210 moves from smaller vasculature into vasculature with a relatively larger cross-sectional area. Without wishing to be bound by any particular theory, it is believed that tissue in the veins and arteries (e.g., endothelial cells) exhibit a different reflectance and absorption spectrum to electromagnetic radiation than tissue in the cavoatrial junction and heart (e.g., muscular tissue cells). It is also believed that a larger volume of blood in larger vasculature attenuates an amount (i.e., an intensity) of backscattered electromagnetic radiation from tissue proximate the distal tip 210. As the distal tip 210 moves into larger vasculature, the distal tip 210 so called "fishtails" wherein the source electromagnetic radiation transmitted through the distal tip 210 is transmitted to vascular walls and tissue at angles other than substantially parallel to the vascular walls and tissue (e.g., at incident angles to the vascular walls and tissue). In some such embodiments, the distal tip 210 receives a relatively increased amount of backscattered electromagnetic radiation at wavelengths that are reflected by the vascular walls and tissue, altering a value of the ratio of the intensity of the backscattered electromagnetic radiation at the first wavelength and the second wavelength. By way of contrast, in smaller vasculature, the source electromagnetic radiation is transmitted at angles that are substantially parallel to vascular walls and, therefore, the distal tip 210 does not receive a substantial amount of electromagnetic radiation backscattered from the vascular walls and tissue. Accordingly, in some embodiments, the ratio of intensities of backscattered electromagnetic radiation at two or more wavelengths may be used to determine a size of vasculature proximate the distal tip 210, which may be particularly useful for determining malposition (or tracking) of the catheter 200. For example, responsive to determining that the cross-sectional area of the vasculature proximate the distal tip 210 is progressively becoming smaller, the computing system 300 may determine that the catheter 200 is being advanced away from the heart.

In other embodiments, the computing system 350 may be configured to determine a diameter, a cross-sectional area, or both of the vasculature of the patient proximate the distal tip 210 of the catheter 200 based, at least in part, on the ratio of the intensity of the source electromagnetic radiation to the intensity of the backscattered electromagnetic radiation. By way of nonlimiting example, the ratio of the intensity of the source electromagnetic radiation to the intensity of the backscattered electromagnetic radiation may decrease as the distal tip 210 advances from vasculature having a smaller cross-sectional area to vasculature having a relatively larger cross-sectional area.

In some embodiments, the computing system 350 is configured to determine a direction of movement of the distal tip 210 relative to a direction of blood flow. In some such embodiments, the computing system 350 may be configured to determine a shift in a wavelength between the source electromagnetic radiation and the backscattered electromagnetic radiation. Stated another way, the computing system 350 may be configured to determine a redshift (e.g., an increase in wavelength) or a blueshift (e.g., a decrease in wavelength) between the source electromagnetic radiation and the backscattered electromagnetic radiation. In some embodiments, where the distal tip 210 is moving in a vein toward the heart 320, the distal tip 210 may be moving in a same direction as deoxygenated blood traveling toward the CAJ 114 (FIG. 1). In some such embodiments, the backscattered electromagnetic radiation may exhibit an increased wavelength compared to the source electromagnetic radiation (e.g., such as, for example, an increase of about 1 nm). When the distal tip 210 is moved against the flow of blood in the vasculature (e.g., countercurrent to the direction of blood flow), such as when the distal tip 210 undesirably moves toward the second vein 118 (FIG. 1) at the first junction 120 (FIG. 1) or toward the third vein 124 (FIG. 1) or the contralateral subclavian vein 126 (FIG. 1) at the second junction 122 (FIG. 1), the backscattered electromagnetic radiation may exhibit a decreased wavelength compared to the source electromagnetic radiation (e.g., such as, for example, a decrease of about 1 nm). Accordingly, the computing system 350 may be configured to determine a direction of movement of the distal tip 210 based on the spectrum or shift in wavelength of the backscattered electromagnetic radiation relative to the CAJ 114 or the heart 100 (FIG. 1).

In other embodiments, the computing system 350 may be configured to determine when the distal tip 210 has passed a junction (e.g., an intersection) between two or more arteries or two or more veins (e.g., the first junction 120 or the second junction 122). In some embodiments, due to a turbulent flow of blood at such junctions, a spectrum of the backscattered electromagnetic radiation may broaden. In other words, the backscattered electromagnetic radiation may exhibit a broader spectrum of wavelengths than when the distal tip 210 is not located proximate a junction in the vasculature. Stated another way, responsive to detecting a broadening of a spectrum of the backscattered electromagnetic radiation, the computing system 350 may be configured to detect when the distal tip 210 has passed a junction. In other embodiments, the computing system 350 may be configured to determine that the distal tip 210 has passed a junction responsive to determining an increase in an intensity of backscattered electromagnetic radiation compared to a baseline intensity of the backscattered electromagnetic radiation. Without wishing to be bound by any particular theory, it is believed that the increase in the intensity of the backscattered electromagnetic radiation is caused by so-called fishtailing of the distal tip 210 wherein the distal tip 210 receives an increased amount of backscattered electromagnetic radiation from vascular walls and tissue due, at least in part, to transmitting source electromagnetic radiation at angles incident to the vascular walls and tissue. Accordingly, the computing system 350 may be configured to determine that the distal tip 210 has passed one or more junctions based, at least in part, on an intensity of backscattered electromagnetic radiation.

The computing system 350 may include digital signal processing configured to determine at least the ratio of a property of the detected electromagnetic radiation that is backscattered by the blood to a like property of the source radiation, the ratio of the intensity of the backscattered electromagnetic radiation at a first wavelength to the intensity of the backscattered electromagnetic radiation at a second wavelength, or both ratios. By way of nonlimiting example, the computing system 350 may include a comparator configured to compare properties of the source electromagnetic radiation (e.g., wavelength, intensity, spectrum, etc.) to properties of the detected electromagnetic radiation.

Although the system 300 has been described as including a fiber optic cable 206 coupled to each of the radiation source 330 and the detector 340, the disclosure is not so limited. In other embodiments, the radiation source 330 comprises any system configured to emit electromagnetic radiation through a catheter and the detector 340 includes any system configured to measure (e.g., detect) electromagnetic radiation proximate a distal end of the catheter. In other words, in some embodiments, the system may not include a fiber optic cable for transmitting or receiving electromagnetic radiation. In some such embodiments, and by way of nonlimiting example, the radiation source 330 may comprise a light-emitting diode (LED) located proximate the distal end of the catheter. The light-emitting diode may comprise a broadband source LED configured to emit white light and, in some embodiments, may emit electromagnetic radiation in the near infrared region. In other embodiments, the LED may comprise a tuned (e.g., monochromatic) LED configured to emit electromagnetic radiation within a predefined range of wavelengths (e.g., red light, violet light, blue light, green light, yellow light, orange light, etc.). A detector may also be located proximate the distal end of the catheter 200. In yet other embodiments, the system 300 may comprise a fiber optic cable 206 extending through at least a portion of the catheter 200, wherein the fiber optic cable 206 is coupled to one or more LEDs and one or more detectors located within the catheter between the proximal and distal ends.

Figure 4:
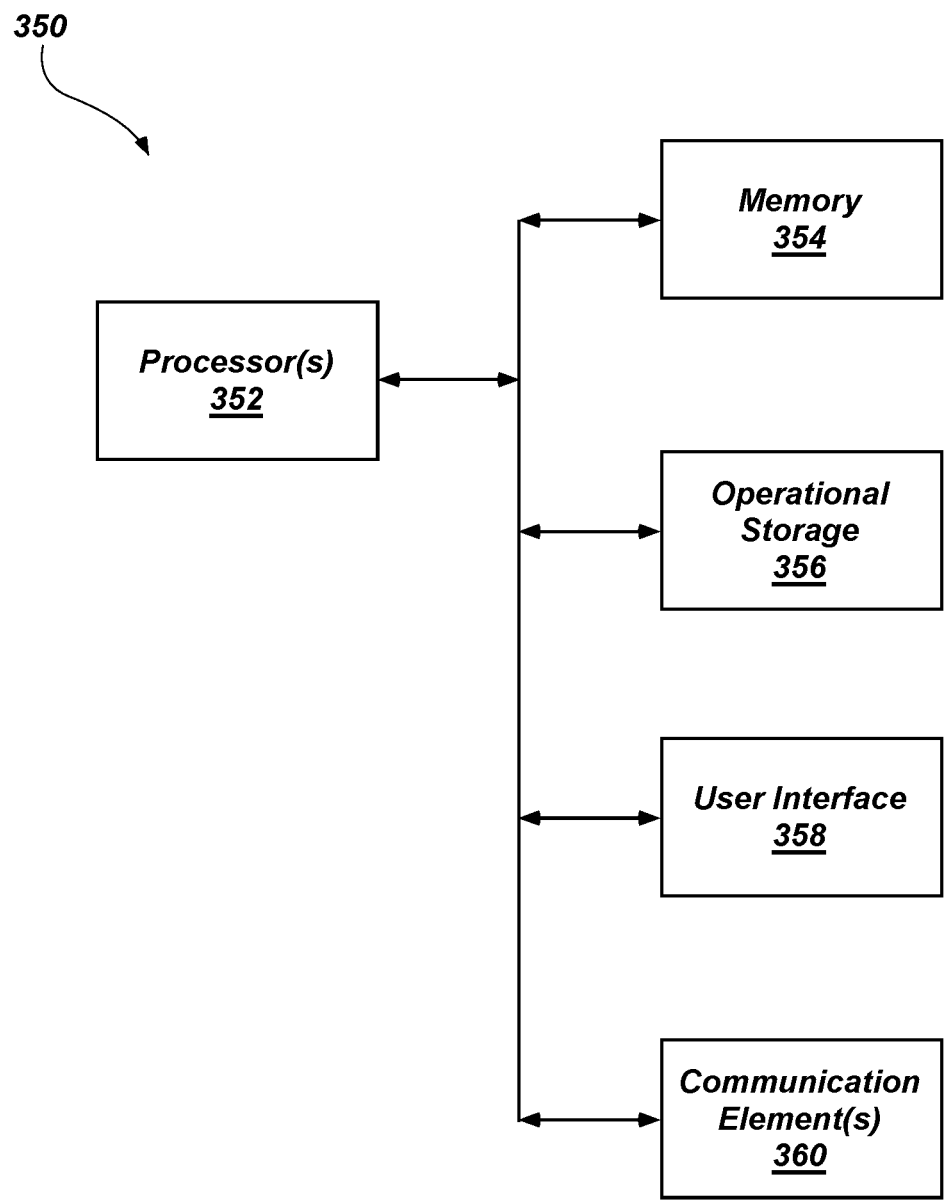
FIG. 4 is a simplified block diagram of a computing system configured for implementing one or more embodiments of the disclosure.

FIG. 4 is a simplified block diagram of the computing system 350 configured for carrying out one or more embodiments of the disclosure. The computing system 350 may be configured to execute software programs containing computing instructions and may include one or more processors 352, one or more memory 354 devices, one or more operational storage 356 devices, one or more user interface 358 devices, and one or more communication elements 360.

The processor 352 may be configured for executing a wide variety of operating systems and applications including the computing instructions for implementing embodiments of the present disclosure. The processor 352 may be configured to control the computing system 350. The processor 352 may be operably coupled to the memory 354, the operational storage 356, the user interface 358, and the communication elements 360. The processor 352 may be configured to receive information from the user interface 358 (e.g., such as from an input device) and the memory 354 and process the data to determine, for example, one or more properties of the catheter 200, such as a location of the distal tip 210 (FIG. 3) of the catheter 200 (FIG. 3) relative to the cavoatrial junction 114 (FIG. 1), a diameter of the vasculature proximate the distal tip 210 of the catheter 200, a direction of movement of the distal tip 210 in the vasculature, whether the distal tip 210 has passed one or more junctions, or a cross-sectional area of the vasculature proximate the distal tip 210. The processor 352 may be configured to receive information (e.g., an intensity of backscattered electromagnetic radiation at one or more wavelengths, a spectrum of backscattered electromagnetic radiation, etc.) from the detector 330, etc. The processor 352 may also be configured to receive information from the memory 354, such as information related to an intensity of the source electromagnetic radiation at one or more wavelengths.

The memory 354 may be used to hold computing instructions, data, and other information for performing a wide variety of tasks including performing embodiments of the present disclosure. By way of example, and not limitation, the memory 354 may include Synchronous Random Access Memory (SRAM), Dynamic RAM (DRAM), Read-Only Memory (ROM), Flash memory, phase change memory, and other suitable information storage devices. The memory 354 may include data related to the catheter 200 (FIG. 3), the source electromagnetic radiation from the radiation source 330 (FIG. 3), and the backscattered electromagnetic radiation detected by the detector 340 (FIG. 3), such as, for example, one or more of a spectrum, a first wavelength, a second wavelength, etc., or an intensity at one or more wavelengths of the source electromagnetic radiation and one or more of a spectrum or an intensity of the backscattered electromagnetic radiation at one or more wavelengths. In some embodiments, the memory 354 may be configured to store information corresponding to the diameter, the cross-sectional area, or both of the vasculature as the distal tip 210 of the catheter is advanced in the patient. Accordingly, in some such embodiments, the processor 352 may be configured to provide a map of at least a relative diameter, a cross-sectional area, or both of the vasculature as the catheter 200 is advanced.

The communication elements 360 may be configured for communicating with other devices or communication networks. By way of example, and not limitation, the communication elements 360 may include elements for communicating on wired and wireless communication media, such as, for example, serial ports, parallel ports, Ethernet connections, universal serial bus (USB) connections IEEE 1394 ("firewire") connections, bluetooth wireless connections, 802.1 a/b/g/n type wireless connections, cellular phone wireless connections and other suitable communication interfaces and protocols.

The operational storage 356 may be used for storing information in non-volatile memory for use in the computing system 350. The operational storage 356 may be configured as one or more storage devices. By way of nonlimiting example, these storage devices may include computer-readable media (CRM). This CRM may include, but is not limited to, magnetic, optical, and solid state storage devices such as disk drives, magnetic tapes, CDs (compact discs), DVDs (digital versatile discs or digital video discs), FLASH memory, and other suitable information storage devices.

The user interface 358 may include input devices and output devices operably coupled to the processor 352. By way of nonlimiting example the input devices may include devices such as a keyboard, a numerical keypad, a mouse, a touchscreen, a button array, a track pad, a remote control, cameras, sensors, a microphone, and combinations thereof. The input devices may be configured to receive commands from the user and present the commands to the processor 352 to perform operations responsive to the commands. The output devices may include, for example, an electronic display such as a light-emitting diode (LED) array, a segmented display, a liquid crystal display, a cathode ray tube display, a plasma display, and other types of electronic displays. The output devices may also include other peripheral output devices, such as speakers, to provide an audible indication of the position of distal tip 210 of catheter 200 or a screen to provide a visual indication of the position of the distal tip 210. In some embodiments, the input devices and the output devices may be integrated in or controlled by the same device, such as, for example, a touchscreen display. In some embodiments, the output device may be configured to display or produce at least one of a signal indicative of a location of the distal tip 210 and one or more recommended actions determined by the computing system 350, such as for example, a recommendation to advance the catheter 200 (FIG. 1), a recommendation to at least partially retract the catheter 200, or a recommendation to stop advancement of the catheter 200. In some embodiments, the user interface 358 may comprise one or more of an electronic display or a speaker configured to provide the recommended action, such as notifying the user whether to advance or stop advancement of the catheter 200.

The processor 352 may be configured to receive from the detector 340 (FIG. 3) an intensity of the detected backscattered electromagnetic radiation at one or more wavelengths (e.g., such as a spectrum of the backscattered electromagnetic radiation). The processor 352 may further be configured to receive information about the source electromagnetic radiation from the memory 354. The processor 352 may be configured to determine a ratio of an intensity of the source electromagnetic radiation to an intensity of the backscattered electromagnetic radiation and compare the ratio to a predetermined value. For example, the ratio may be determined according to Equation (1) below:

$$R_I = I_s/I_d \qquad \text{Equation (1)},$$

wherein $R_I$ is the ratio, $I_s$ is the intensity of the source electromagnetic radiation, and $I_d$ is the intensity of the backscattered electromagnetic radiation. The memory 354 and the operational storage 356 may be configured to retain information related to the source electromagnetic radiation (e.g., the intensity of the source electromagnetic radiation) and the detected electromagnetic radiation (e.g., the intensity of the detected electromagnetic radiation). The processor 352 may be configured to determine the ratio using the information stored in the memory 354 and the operational storage 356.

When the distal tip 210 (FIG. 3) of the catheter 200 (FIG. 3) is disposed along a venous wall during insertion, the value of the ratio $R_I$ using Equation (1) may be equal to about 10. When the distal tip 210 approaches the cavoatrial junction 114 (FIG. 1), the value of this ratio may decrease significantly and may be equal to less than about 5, less than about 4, or even less than about 3. In some embodiments, the value of the ratio may be at least about two times less, or even at least about three times less when the distal tip 210 is proximate the cavoatrial junction 114 than when it is not. As described herein, the value of the ratio $R_I$ refers to the value defined in Equation (1). Of course, and as described above, it is contemplated that the ratio may be equal to the inverse of Equation (1). It is understood that one of ordinary skill in the art would understand that in some such embodiments the values of the ratio $R_I$ described herein would be the inverse of the values described herein (e.g., rather than being equal to 10, the ratio would be equal to 0.1).

In some embodiments, the value of the ratio $R_I$ may be affected by beating of the heart. For example, during diastole, an intensity of the backscattered electromagnetic radiation may increase as the ventricles open. An intensity of the backscattered electromagnetic radiation may decrease as the ventricles contract during systole. In some embodiments, a ratio of the intensity of the backscattered electromagnetic radiation during diastole to an intensity of the backscattered electromagnetic radiation during systole may be between about 5 and about 6. Such large and relatively rapid variations in intensity facilitate determination when the distal tip of the advancing catheter approaches the exit of the cavoatrial junction 114 into the right atrium 108 (FIG. 1) of the heart.

In other embodiments, the processor 352 may be configured to determine a location of the distal tip 210 (FIG. 3) of the catheter 200 (FIG. 3) relative to the cavoatrial junction 114 (FIG. 1) based on a relative intensity between at least two wavelengths of backscattered electromagnetic radiation. The two wavelengths may be selected to exhibit a different reflectance by tissue in veins or arteries (e.g., in the superior vena cava) than the tissue in the right atrium. By way of nonlimiting example, at least one wavelength may exhibit a relatively larger reflectance by tissue veins or arteries than tissue in the cavoatrial junction and at least another wavelength may exhibit a relatively smaller reflectance by tissue in the veins and arteries than tissue in the cavoatrial junction. In some such embodiments, the processor 352 may be configured to determine a ratio of an intensity of backscattered electromagnetic radiation of at least a first wavelength (e.g., at least a first substantially monochromatic wavelength) to an intensity of backscattered electromagnetic radiation of at least a second wavelength (e.g., at least a second substantially monochromatic wavelength). The at least a first wavelength and the at least a second wavelength may be substantially similar to at least a first wavelength and at least a second wavelength of source electromagnetic radiation provided by the radiation source 330 (FIG. 3). The ratio of the backscattered electromagnetic radiation may be determined according to Equation (2) below:

$$R_b = I_{\lambda 1}/I_{\lambda 2} \qquad \text{Equation (2),}$$

wherein $R_b$ is the ratio of the backscattered electromagnetic radiation, $I_{\lambda 1}$ is the intensity of the backscattered electromagnetic radiation at the at least a first substantially monochromatic wavelength, and $I_{\lambda 2}$ is the intensity of the backscattered electromagnetic radiation at the at least a second substantially monochromatic wavelength. As described herein, the value of the ratio $R_b$ refers to the value defined in Equation (2). Of course, and as described above, it is contemplated that the ratio may be equal to the inverse of Equation (2). It is understood that one of ordinary skill in the art would understand that in some such embodiments the values of the ratio $R_b$ described herein would be the inverse of the values described herein.

The position of the distal tip 210 relative to the cavoatrial junction 114 may be determined with substantial accuracy based on the value of one or both of the ratios, $R_I$ or $R_b$. For example, the value of $R_I$ may be used to estimate a relative location of the distal tip 210 relative to the cavoatrial junction 114. Without wishing to be bound by any particular theory, it is believed that when the catheter 200 is disposed within the veins and arteries, the distal tip 210 is disposed proximate vascular walls. When the source electromagnetic radiation is transmitted to the distal tip 210, a relatively large proportion of the electromagnetic radiation is attenuated through the vascular walls, reducing an amount of the electromagnetic radiation that is backscattered by the blood. On the other hand, when the distal tip 210 approaches an opening in the vasculature, which may also be characterized as an enlarged volume, such as the cavoatrial junction 114, the cross-sectional area of the vasculature (e.g., the veins, the arteries, etc.) increases. As the cross-sectional area increases, the source electromagnetic radiation is backscattered by more reflectors (e.g., red blood cells) than when the distal tip 210 is in the vasculature (e.g., the veins, the arteries, etc.) having a smaller cross-sectional area (e.g., prior to approaching the cavoatrial junction 114). Accordingly, because there are a larger number of backscatterers proximate the cavoatrial junction 114, the detected backscattered electromagnetic radiation rapidly exhibits a higher intensity when the distal tip 210 is proximate the cavoatrial junction 114 than when the distal tip 210 is disposed in a vein or artery. Stated another way, the detected backscattered electromagnetic radiation may be directly related to a volume of blood proximate the distal tip 210. For example, the larger the vessel into which the electromagnetic radiation is emitted, the larger the volume of red blood cells and the associated point cloud and, therefore, the larger the intensity of the backscattered electromagnetic radiation. Due to the relatively sudden, increased intensity of the backscattered electromagnetic radiation when the distal tip 210 is proximate the cavoatrial junction 114, the location of the distal tip 210 relative to the cavoatrial junction 114 may be determined based on the value of the ratio.

In addition, the location of the distal tip 210 relative to the cavoatrial junction may be determined based, at least in part, on the ratio $R_b$. Without wishing to be bound by any particular theory, it is believed that vascular walls (e.g., such as in the veins, the arteries, and the superior vena cava) appear lighter in color due to the presence of collagen and endothelial cells in those portions of the vasculature, while tissue proximate the cavoatrial junction 114 exhibits a darker color than the vascular walls. A color of the tissue in the vasculature may transition from a white color in the veins and arteries to a pink color in the superior vena cava, and to a red color at the cavoatrial junction. Accordingly, the different colors exhibited by the vascular walls and the tissue proximate the cavoatrial junction 114 may absorb or reflect different wavelengths, and at different intensities, of electromagnetic radiation. Stated another way, the different tissues in the vasculature leading up to the cavoatrial junction 114 may exhibit a different reflectance at different wavelengths or at a given wavelength. In addition, it is believed that as the distal tip 210 approaches a larger cavity from a relatively smaller cross-sectional area (e.g., as the distal tip 210 approaches the cavoatrial junction 114), the distal tip 210 so called "fishtails" as it is moves from substantially parallel to the vascular walls to angles other than parallel to the tissue in the vasculature. Since the distal tip 210 moves to angles that are incident to the tissue in the vasculature, the distal tip 210 receives an increased amount of backscattered electromagnetic radiation that is detected by the detector 340. Accordingly, as the distal tip 210 of the catheter approaches a relatively larger junction, the distal tip 210 receives an increased intensity of backscattered electromagnetic radiation.

In addition, an amount of the backscattered electromagnetic radiation may increase when the distal tip 210 is located in vasculature (e.g., a vein or artery) having a larger cross-sectional area compared to when the distal tip 210 is located in vasculature having a relative smaller cross-sectional area. As described above, in some embodiments, it is believed that the increased intensity of the backscattered electromagnetic radiation may be caused by so-called "fishtailing" of the distal tip 210 wherein source electromagnetic radiation is transmitted and backscattered electromagnetic radiation is received at angles that are incident to tissue in the vasculature proximate the vasculature. In some embodiments, a diameter, a cross-sectional area, or both of the vasculature (e.g., a vein, an artery, etc.) surrounding and proximate the distal tip 210 may be estimated based on a value of an intensity of the backscattered electromagnetic radiation at one or more wavelengths compared to a baseline value of the intensity of the backscattered electromagnetic radiation. Since a diameter and cross-sectional area of the vasculature of any given patient increases from, for example, the arm to the cavoatrial junction 114, a relative location of the distal tip 210 may also be estimated based on the value of one or both of $R_I$ or $R_b$. As noted above, a side fire fiber optic cable 270 as illustrated in FIG. 2H may be particularly suitable for this application.

In some embodiments, the processor 352 may be further configured to determine a location of the distal tip 210 (FIG. 3) based on the spectrum of the backscattered electromagnetic radiation. The backscattered electromagnetic radiation spectra may be different when the distal tip 210 is in the veins or arteries compared to when the distal tip 210 approaches the cavoatrial junction 114 (FIG. 1). In some embodiments, the processor 352 may be configured to compare a spectrum of backscattered electromagnetic radiation to one or more spectral patterns stored in the memory 354 (FIG. 4) of backscattered radiation when the distal tip 210 is in the vasculature or in the cavoatrial junction. In some embodiments, the processor 352 may be configured to compare an intensity of backscattered electromagnetic radiation at one or more wavelengths (e.g., at two wavelengths) to values stored in, for example, a look-up table in the memory 354 to determine a location of the distal tip 210. Stated another way, one or more properties of the catheter (e.g., a location of the distal tip 210) may be determined based on a comparison of the intensity of the backscattered electromagnetic radiation (e.g., an intensity thereof at one wavelength, at two wavelengths, etc.) to values stored in a look-up table. As described above and without wishing to be bound by any particular theory, it is believed that the different tissue in the vascular cells (e.g., the vascular endothelial cells on the vascular walls) compared to the tissue in the cavoatrial junction (e.g., muscular tissue cells) reflect different wavelengths of electromagnetic radiation and at different intensities. Accordingly, the processor 352 may be configured to determine a change in the spectrum of the backscattered electromagnetic radiation detected by the detector 340, which may be used to determine a location of the distal tip 210 relative to the cavoatrial junction 114.

Accordingly, based on one or more of the value of the ratio of the intensity of the source electromagnetic radiation to the intensity of the backscattered electromagnetic radiation (e.g., $R_I$), the spectrum of the backscattered electromagnetic radiation in view of the source radiation spectrum, the ratio of backscattered electromagnetic radiation of at least a first wavelength to an intensity of backscattered electromagnetic radiation of at least a second wavelength (e.g., $R_b$), or the spectrum of the backscattered electromagnetic radiation, the processor 352 may be configured to determine whether the catheter 200 (FIG. 3) should be further advanced or whether advancement thereof should be halted. By way of nonlimiting example, responsive to determining the value of the ratio $R_1$, the processor 352 may be configured to determine whether the ratio is less than a predetermined number (e.g., less than about 5, less than about 4, less than about 3, etc.). If the value of the ratio $R_I$ is less than the predetermined number, the processor 352 may provide an instruction or a signal to one or both of the communication elements 360 and the user interface 358 to stop advancement of the catheter. As another nonlimiting example, the processor 352 may be configured to determine an amount by which the ratio $R_b$ has changed responsive to advancement of the distal tip by a predetermined distance (e.g., 1 mm, 2 mm, etc.). Responsive to determining that the ratio $R_I$ is less than the predetermined number, that the ratio $R_b$ has changed by a predetermined value (e.g., more than about 30 percent, more than about 40 percent, etc.), or that a value of $R_b$ falls within a predetermined range, the user interface 358 may be configured to receive, from the processor 352, instructions to provide an indication to the user to stop advancement of the catheter 200. In some embodiments, the user interface 358 may comprise an output device configured to provide a signal indicative of the location of the distal tip 210. By way of nonlimiting example, the user interface 358 may be configured to display a red light (indicating to the user that the catheter 200 should not be advanced further) when the ratio $R_I$ is less than the predetermined number or when the ratio $R_b$ falls within a predetermined range of values or exhibits a substantial change (e.g., a change greater than about 20 percent, a change greater than about 30 percent, a change greater than about 40 percent etc.) responsive to advancement of the catheter 200, and configured to display a green light (indicating to the user that the catheter 200 may continue to be advanced) when $R_I$ is greater than the predetermined number or when $R_b$ falls outside the predetermined range of numbers or changes by less than the predetermined amount responsive to advancement of the catheter 200. In other embodiments, the output device comprises a speaker configured to provide a variable tone to notify the user whether to advance or stop advancement of the catheter 200.

In yet additional embodiments, the processor 352 may be configured to determine a direction of movement of the distal tip 210 (FIG. 3). By way of nonlimiting example, the processor 352 may be configured to determine a direction of movement of the distal tip 210 based on a value or an increase in an intensity of backscattered electromagnetic radiation.

Figure 5A:
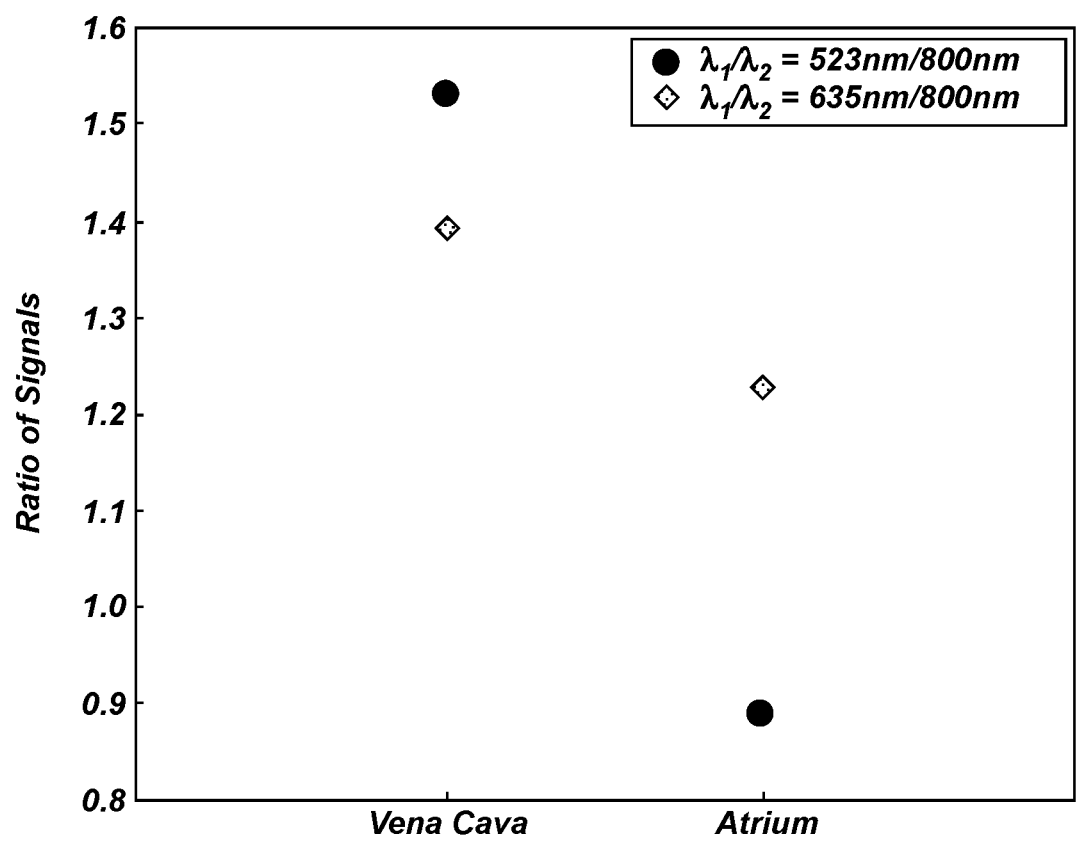
FIG. 5A is a graph illustrating a ratio of an intensity of backscattered electromagnetic radiation at a first wavelength to an intensity of backscattered electromagnetic radiation at a second wavelength while reflecting from different tissue types.

FIG. 5A is a graph illustrating a ratio (i.e., $R_b$, as defined in Equation (2) above) of an intensity of backscattered electromagnetic radiation at a first wavelength to an intensity of the backscattered electromagnetic radiation at a second wavelength when a distal tip 200 of a catheter 200 is located in the superior vena cava and when the distal tip 200 is located in the right atrium of a heart. As illustrated, the ratio of the backscattered electromagnetic radiation differs when the distal tip 210 is in the superior vena cava compared to when the distal tip 210 is in, for example, the right atrium. In addition, in some embodiments, a difference between the value of the ratio is larger when the first wavelength and second wavelength are about 523 nm and about 800 nm, respectively compared to when the first and second wavelength are about 635 nm and about 800 nm, respectively. In some embodiments, the first and second wavelength may be selected such that a difference in the value of the ratio when the distal tip 210 is in the superior vena cava compared to when the distal tip 210 is in the right atrium is maximized. Stated another way, the first wavelength may be selected to exhibit a relatively higher reflectivity to tissue in the veins and arteries than to the muscular tissue in the cavoatrial junction. In some embodiments, the second wavelength may be selected to exhibit a relatively higher reflectivity to tissue in the cavoatrial junction than to tissue in the veins and arteries.

Figure 5B:
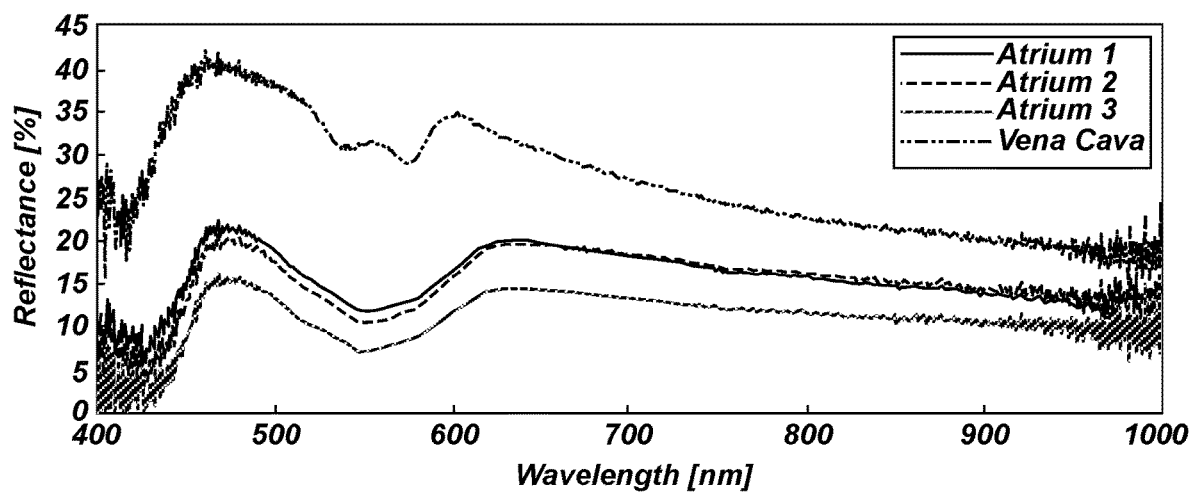
FIG. 5B is a graph showing a percent of electromagnetic radiation reflected as a function of wavelength in each of the superior vena cava and in the right atrium.

FIG. 5B is a graph showing a percentage of electromagnetic radiation reflected (i.e., a reflectance) as a function of wavelength in each of the superior vena cava and at three locations in the right atrium. As illustrated, a difference in an amount of reflectance is greater between the superior vena cava and the right atrium at lower wavelengths (e.g., between about 450 nm and about 550 nm) than at greater wavelengths (e.g., between about 750 nm and about 950 nm). Stated another way, at wavelengths between about 450 nm and about 550 nm, an amount (e.g., a percentage) of electromagnetic radiation reflected in the veins (e.g., the superior vena cava) and arteries may be substantially greater than a percentage of electromagnetic radiation backscattered in the cavoatrial junction. At wavelengths between about, for example, 750 nm and about 850 nm, a difference in a percentage of electromagnetic radiation reflected by the veins and arteries relative to the cavoatrial junction is less than that at wavelengths between about 450 nm and about 550. In some embodiments, using at least two wavelengths, a location of the distal tip may be determined based on a ratio of the reflectance between at least a first wavelength and at least a second wavelength (e.g., $R_b$). In some embodiments, using the at least two wavelengths may normalize the measured values and increase a signal to noise ratio (SNR) of the system.

Figure 5C:
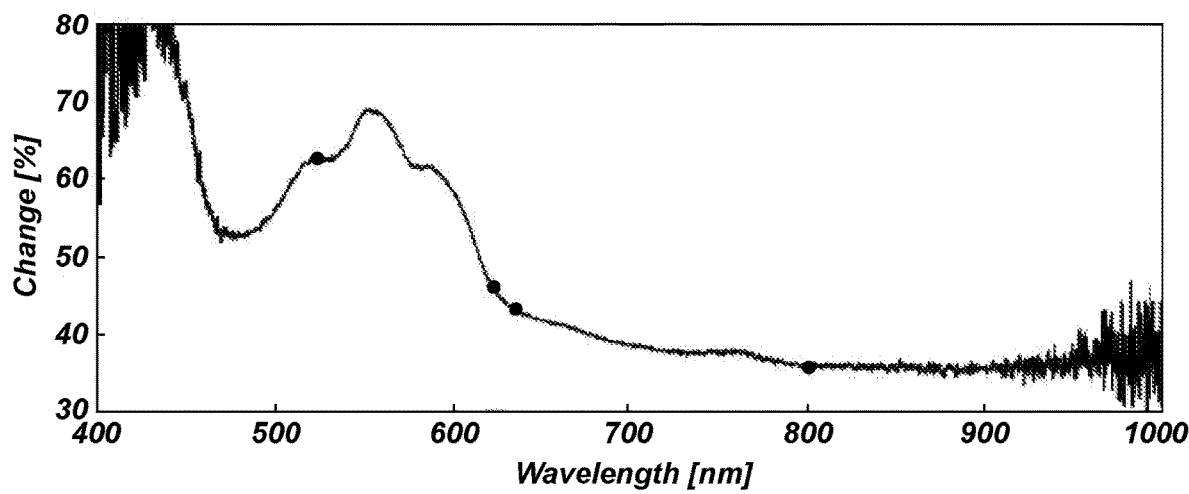
FIG. 5C is a graph showing a degree of difference in backscattered electromagnetic radiation between the vascular walls in the superior vena cava and the tissue in the atrium of the heart.

FIG. 5C is a graph showing a degree of difference in backscattered electromagnetic radiation between the vascular walls in the superior vena cava and the tissue in the atrium of the heart (e.g., proximate the cavoatrial junction). FIG. 5C graphically illustrates a difference between a reflectance of electromagnetic radiation reflected by the superior vena cava and the right atrium at wavelengths between about 400 nm and about 1,000 nm. The ratio of the reflectance was calculated according to Equation (3) below:

$$R_r = (1 - (R_{ra}/R_{vc}))/100 \quad \text{Equation (3)},$$

wherein $R_{ra}$ is the average reflectance by the right atrium at three locations (illustrated in FIG. 5B), $R_{vc}$ is the reflectance by the superior vena cava, and $R_r$ is the ratio of reflectance graphically illustrated in FIG. 5C. As illustrated in the graph, there is a substantially greater difference in an amount of backscattered electromagnetic radiation between the vascular walls and the tissue in the heart at wavelengths between about 450 nm and about 650 nm than at higher wavelengths, such as, for example, between about 750 nm and about 950 nm. At wavelengths greater than about 800 nm, the ratio of the reflectance begins to stabilize and does not substantially change with a change in wavelength. Accordingly, in some embodiments, a first wavelength may be selected to be between about 450 nm and about 650 nm and a second wavelength may be selected to be between about 750 nm and about 950 nm.

Figure 5D:
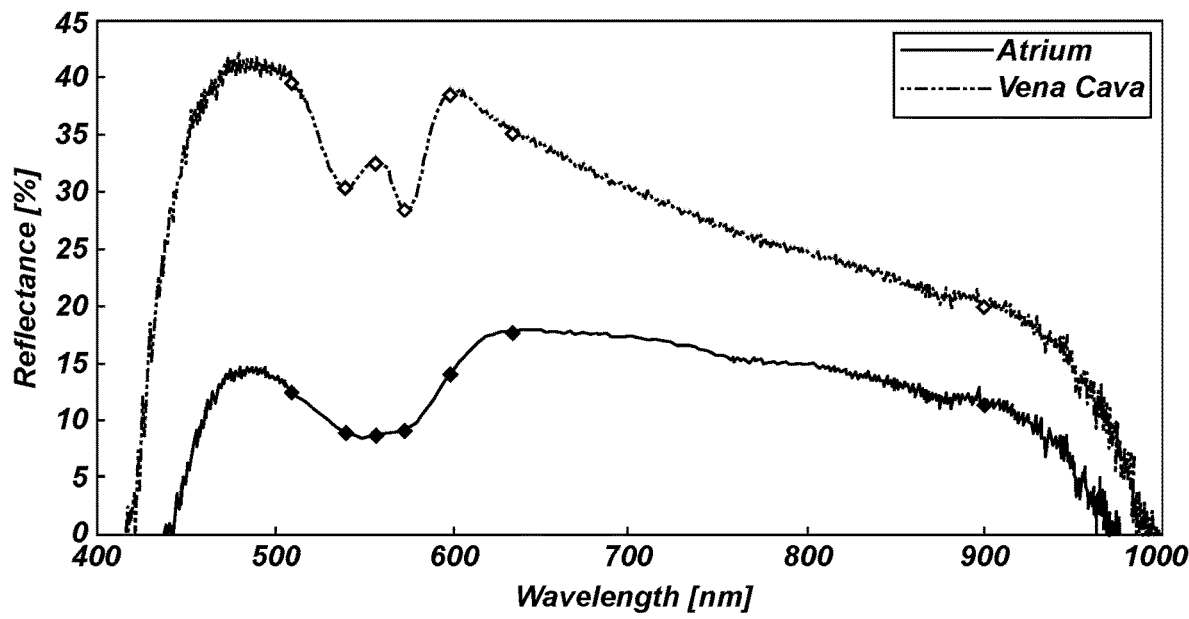
FIG. 5D is a graph showing a percentage of electromagnetic radiation that is reflected as a function of wavelength in the right atrium and the superior vena cava.

FIG. 5D is a graph showing a percentage of electromagnetic radiation that is reflected as a function of wavelength in the right atrium and the superior vena cava in another example. A difference between a reflectance of electromagnetic radiation in the superior vena cava and a reflectance of electromagnetic radiation in the right atrium may vary depending on the wavelength. At wavelengths between about 450 nm and about 650 nm, such as between about 500 nm and about 600 nm, the difference may be substantially greater than at wavelengths between about 750 nm and about 950 nm, such as between about 800 nm and about 900 nm. The diamond shapes in FIG. 5D are at wavelengths of electromagnetic radiation that may be produced by commercially available lasers.

By way of nonlimiting example a ratio between a reflectance at a first wavelength and a reflectance at a second wavelength may be determined to determine a location of the distal tip of the catheter relative to the cavoatrial junction. Assuming that the first wavelength is selected to be about 500 nm and the second wavelength is selected to be about 800 nm, when the distal tip is in the superior vena cava, the ratio $R_b$ may be equal to about 1.6 (i.e., 40/25, since at about 500 nm, the reflectance in the superior vena cava is equal to about 40 percent and at a wavelength of about 800 nm, the reflectance in the superior vena cava is equal to about 25 percent). When the distal tip is advanced to a location proximate the right atrium, the ratio may be equal to about 0.93 (i.e., 14/15, since at a wavelength of about 500 nm, the reflectance in the right atrium is equal to about 14 percent and at a wavelength of about 800 nm, the reflectance in the right atrium is equal to about 15 percent). Of course, one of ordinary skill in the art would understand that the value of the ratios described above may be the inverse of those described (i.e., about 0.625 (25/40) and about 1.07 (15/14), depending on which wavelength is selected to be the first wavelength and the second wavelength).

Figure 5E:
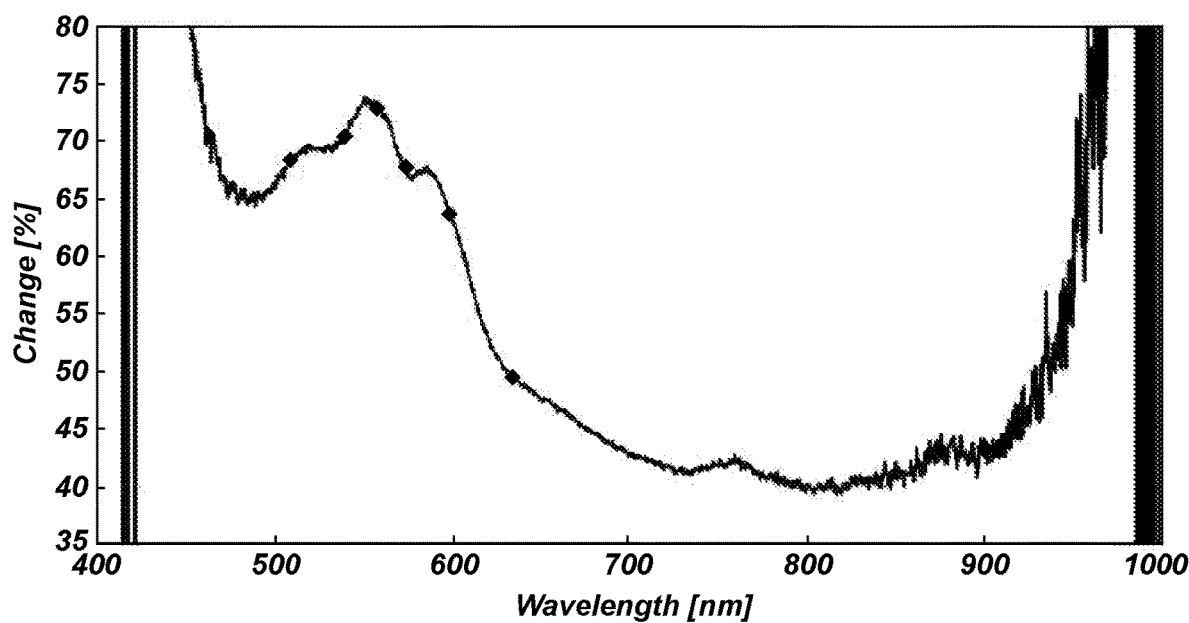
FIG. 5E is a graph showing a relative difference in an amount of electromagnetic radiation that is reflected by the superior vena cava and the right atrium as a function of wavelength.

FIG. 5E is a graph showing a relative difference in an amount of electromagnetic radiation that is reflected by the superior vena cava and the right atrium as a function of wavelength. The plot in FIG. 5E was obtained according to Equation (4) below:

$$\text{Percent Change} = (R_{vc} - R_{ra})/R_{vc} * 100 \quad \text{Equation (4)},$$

wherein $R_{vc}$ and $R_{ra}$ are the reflectance by the superior vena cava and the reflectance by the right atrium shown in FIG. 5D, respectively.

Figure 6:
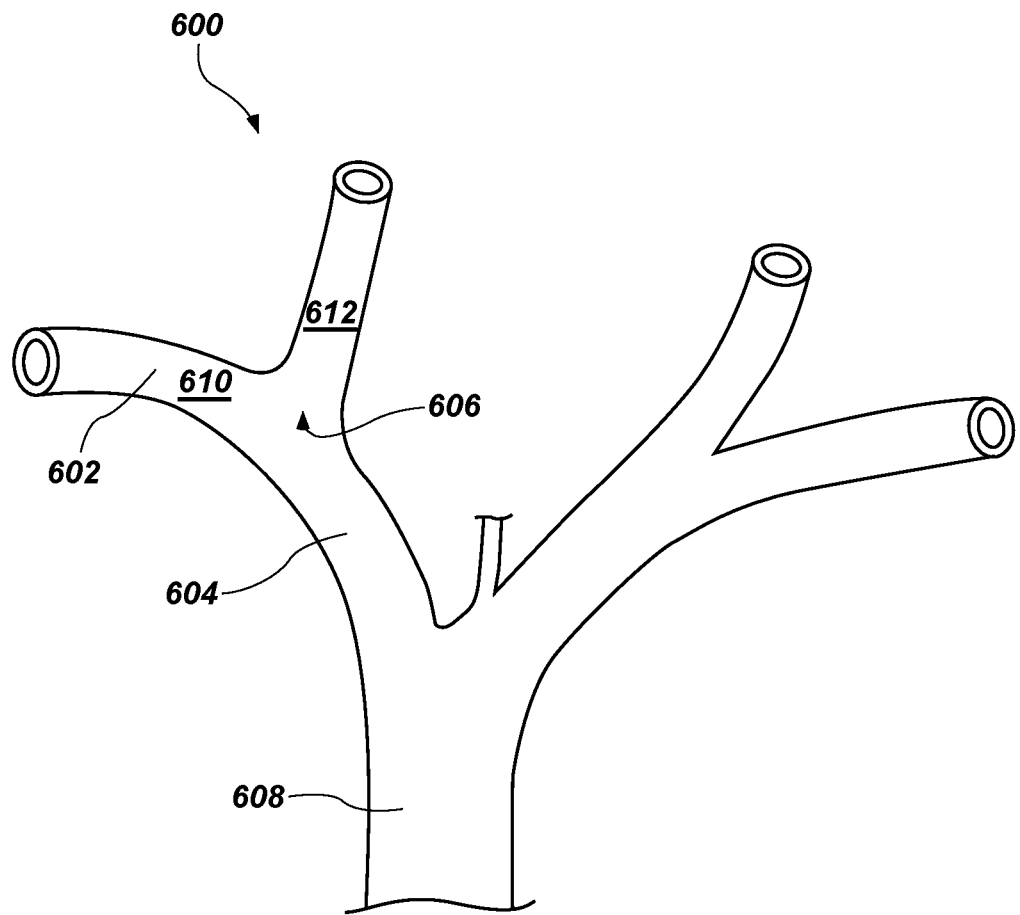
FIG. 6 is a simplified cross-sectional view of a section of vasculature 600.

FIG. 6 is a simplified cross-sectional view of a section of vasculature 600. The vasculature 600 may include a first region 602 having a relatively smaller inner diameter than other regions thereof, a second region 606 at an intersection of two separate passageways 610, 612 (e.g., two veins, two arteries, etc.), a third region 604 having a larger inner diameter than the first region 602 and the second region 606, and a fourth region 608 having a larger inner diameter than the second region 606 and the third region 604. In some embodiments, the fourth region 608 may be proximate the cavoatrial junction. By way of nonlimiting example, as a catheter in inserted from the first region 602 toward the second region 606, a value of $R_I$ may decrease (since an intensity of backscattered electromagnetic radiation may increase in vasculature having a relatively larger cross-sectional area). Stated another way, the value of $R_I$ may be smaller when the distal tip is located in the second region 606 than when the distal tip is located in the first region 602. During advancement of the catheter from the first region 602 to the second region 606, a wavelength having a peak intensity of the backscattered electromagnetic radiation may be higher than the wavelength having a peak intensity of the source electromagnetic radiation (i.e., the backscattered electromagnetic radiation may exhibit a redshift). A value of the ratio $R_b$ may remain substantially constant since a color of tissue on the vein or artery proximate the distal tip (and, therefore, a reflectance therefrom) may remain substantially the same.

As the distal tip of the catheter is advanced from the second region 606 to the third region 604, the value of $R_I$ may decrease relative to the value of $R_I$ when the distal tip of the catheter is in the second region 606. When the distal tip of the catheter is in the third region 604, a spectrum of the backscattered electromagnetic radiation may broaden (which may be caused by turbulence of blood flow in the third region 604). During advancement of the catheter from the second region 606 to the third region 604, the backscattered electromagnetic radiation may exhibit a redshift since the distal tip is advanced in the same direction as the blood. A value of the ratio $R_b$ may remain substantially constant as the catheter is advanced from the second region 606 to the third region 604.

Responsive to advancing the distal tip of the catheter from the third region 604 to the fourth region 608, the value of $R_I$ may decrease relative to the value of $R_I$ when the distal tip is in the third region 604. In some embodiments, $R_I$ may decrease to a value below about 5. Similarly, as the distal tip of the catheter is advanced to the fourth region 608, the value of $R_b$ may change relative to the value of $R_b$ when the distal tip is in first region 602, the second region 606, or the third region 604 by at least about 5 percent, at least about 10 percent, at least about 20 percent, at least about 30 percent, at least about 40 percent responsive to advancing catheter. In some embodiments, the value of $R_b$ may fall within a predetermined range, such as between about 0.20 and about 0.30, such as between about 0.24 and about 0.28. In other embodiments, the value of $R_b$ may fall between about 0.8 and about 1.2, such as between about 0.9 and about 1.1, responsive to advancing the distal tip to the fourth region 608. During advancement of the catheter from the third region 604 to the fourth region 608, the backscattered electromagnetic radiation may exhibit a redshift.

Figure 7:
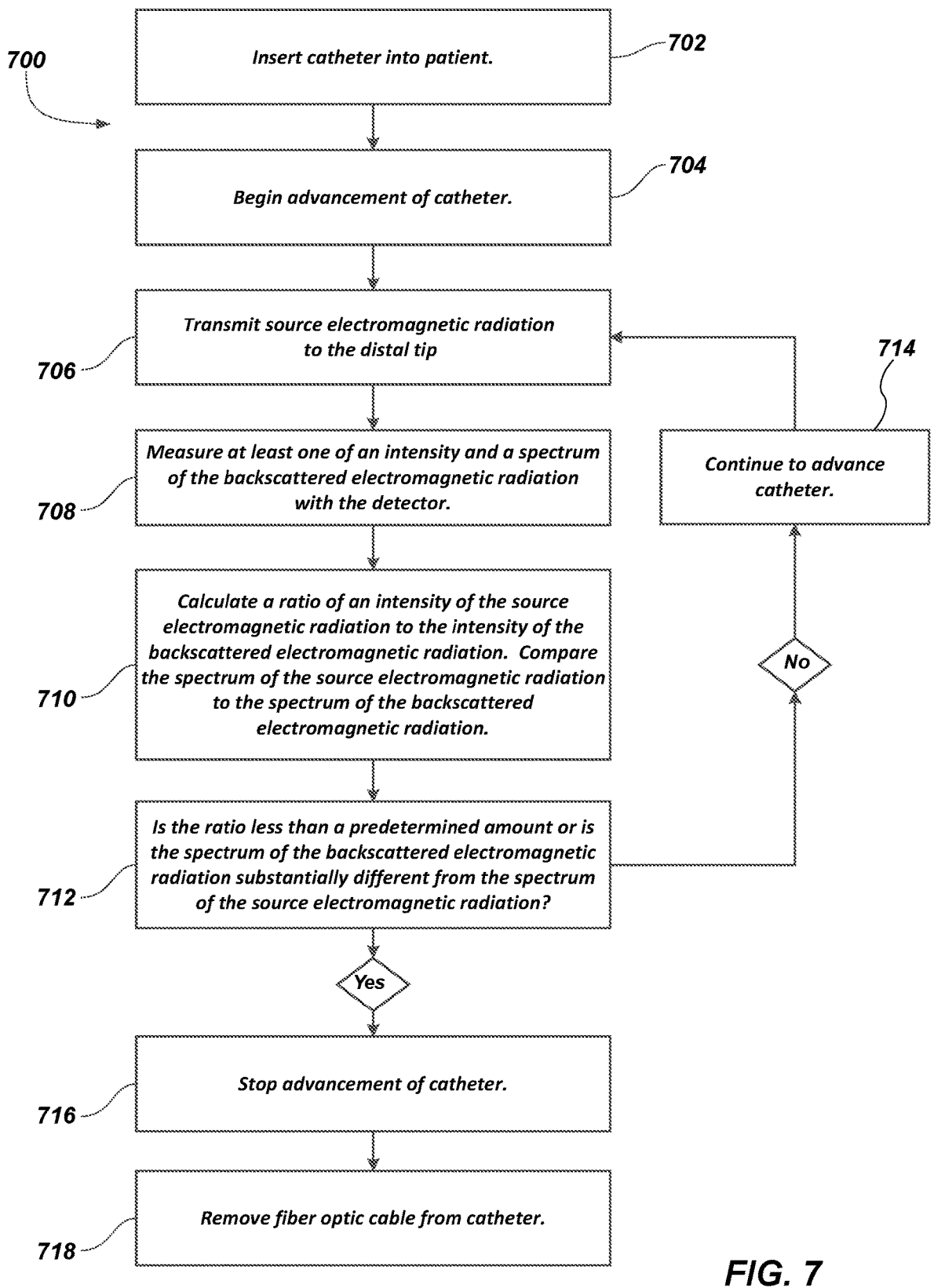
FIG. 7 is a simplified flow diagram depicting a method of determining a location of a distal tip of a catheter relative to the cavoatrial junction of a patient, according to an embodiment of the disclosure.

FIG. 7 is a simplified flow chart illustrating a method 700 of inserting a catheter, according to an embodiment of the disclosure. At operation 702, a catheter is inserted into a patient, such as in an arm of the patient. The catheter may be inserted into the vasculature of the patient, such as into a vein or into an artery. The catheter may include the catheter 700 described above with reference to FIG. 2A through FIG. 2D. For example, the catheter may include at least one fiber optic cable extending therethrough, the fiber optic cable coupled to a radiation source and a detector.

At operation 704, the catheter is advanced at least partially into the patient's vasculature and may be advanced toward the patient's heart (e.g., toward the cavoatrial junction).

At operation 706, source electromagnetic radiation from the radiation source is transmitted to the distal tip of the catheter and to the patient's blood. The electromagnetic radiation may be provided at a substantially monochromatic wavelength and may be polarized. In some embodiments, the source electromagnetic radiation has a wavelength between a wavelength of red light in the visible spectrum and a wavelength in the near-infrared region of the electromagnetic region, such as between about 685 nm and about 1,100 nm. In some embodiments, the source electromagnetic radiation is transmitted to the distal tip of the catheter through the at least one fiber optic cable.

As described above, at least a portion of the source electromagnetic radiation transmitted to the blood may be absorbed by the blood and at least another portion of the source electromagnetic radiation may be scattered (e.g., reflected) by the blood. At operation 708, at least one of a spectrum or an intensity of the backscattered electromagnetic radiation may be detected by the detector coupled to the fiber optic cable. Measuring a spectrum of the backscattered electromagnetic radiation may include determining a shift in a peak wavelength between the source electromagnetic radiation and the backscattered electromagnetic radiation. Due to attenuation and backscattering of the electromagnetic radiation in the blood, the reflected electromagnetic radiation may exhibit a spectrum and an intensity that is different than a spectrum and an intensity of the source electromagnetic radiation.

At operation 710, the ratio of an intensity of the electromagnetic radiation transmitted at operation 706 to an intensity of the backscattered electromagnetic radiation measured at operation 708 is determined. In addition or as an alternative approach, operation 710 may include measuring a spectrum of the backscattered electromagnetic radiation and determining whether there has been a shift in the spectrum of the backscattered electromagnetic radiation relative to the source electromagnetic radiation.

At operation 712 it is determined whether the ratio is less than a predetermined value, if the backscattered spectrum is different than the spectrum of the source electromagnetic radiation, or both (e.g., if there is a blueshift or a redshift). If the ratio is greater than the predetermined value, or if the backscattered spectrum is substantially similar to the spectrum of the source electromagnetic radiation, the method proceeds to operation 714, where the catheter is further advanced through the vascular system. If there is a blueshift in the electromagnetic radiation, the catheter may have undesirably entered a vein (e.g., the subclavian vein) and may be traveling away from the CAJ 114 (FIG. 1). In some such embodiments, the catheter may be at least partially retracted prior to continuing advancement thereof. If there is a redshift in the electromagnetic radiation, the catheter may be travelling in a desired direction toward the CAJ 114. Accordingly, determining a shift in a wavelength of the backscattered electromagnetic radiation relative to a wavelength of the source electromagnetic radiation may serve as a cross-check for the clinician to ensure that the distal tip 210 is moving in the proper direction.

Operations 706, 708, 710, and 712 may be repeated until the ratio is less than the predetermined value, the spectrum of the backscattered electromagnetic radiation is substantially different than the spectrum of the source electromagnetic radiation, or both. When the ratio is less than the predetermined value or the spectrum of the backscattered electromagnetic spectrum is different, the method proceeds to operation 716 where insertion of the catheter is stopped. Use of both techniques may provide a cross-check for the clinician to ensure the catheter distal tip 210 is properly placed. In yet additional embodiments, act 712 may include determining a diameter, a cross-sectional area, or both of the vasculature proximate the distal tip 210 of the catheter based on the value of the ratio. The determined diameter may serve as a cross-check for the clinician to ensure that the catheter distal tip 210 is properly placed. For example, depending on the patient, the diameter or cross-sectional area may be used to determine whether the catheter tip is proximate the cavoatrial junction Operation 718 includes removing the fiber optic cable from the catheter after the catheter has successfully been placed in the patient.

Figure 8:
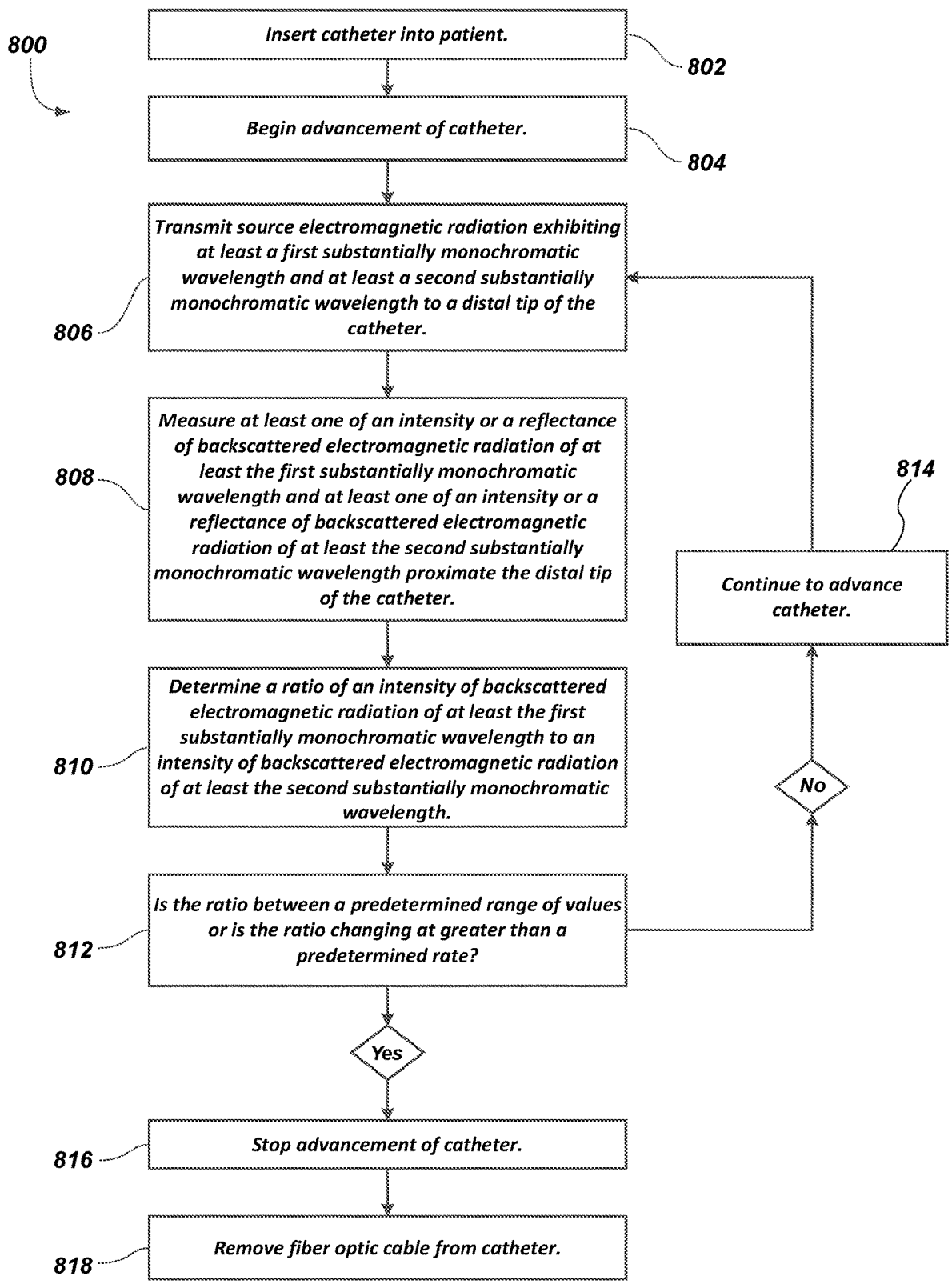
FIG. 8 is a simplified flow chart illustrating a method of inserting a catheter into a patient, according to another embodiment of the disclosure.

FIG. 8 is a simplified flow chart illustrating a method 800 of inserting a catheter into a patient, according to an embodiment of the disclosure. At operation 802, a catheter is inserted into a patient, such as in an arm of the patient. The catheter may be inserted into the vasculature of the patient, such as into a vein or into an artery. The catheter may include the catheter 200 described above with reference to FIG. 2A through FIG. 2D. For example, the catheter 200 may include at least one fiber optic cable extending therethrough, the fiber optic cable coupled to a radiation source and a detector.

At operation 804, the catheter is advanced at least partially into the patient's vasculature and may be advanced toward the patient's heart (e.g., toward the cavoatrial junction).

At operation 806, source electromagnetic radiation is transmitted from the radiation source to a distal tip of the catheter. In some embodiments, the source electromagnetic radiation is transmitted to the distal tip of the catheter through the at least one fiber optic cable. In some embodiments, the source electromagnetic radiation may exhibit at least two distinct wavelengths. By way of nonlimiting example, the source electromagnetic radiation may exhibit at least a first substantially monochromatic wavelength and at least a second substantially monochromatic wavelength. The first substantially monochromatic wavelength may be between about 450 nm and about 650 nm and the second substantially monochromatic wavelength may be between about 750 nm and about 950 nm. In some embodiments, the first substantially monochromatic wavelength may be about 525 nm or about 635 nm and the second substantially monochromatic wavelength may be about 800 nm or about 832 nm. The first wavelength may be selected to exhibit a greater reflectance by the tissue in the veins or arteries than the tissue in the cavoatrial junction and the second wavelength may be selected such that a reflectance by the tissue in the veins or arteries is similar to a reflectance from the tissue in the cavoatrial junction. Of course, it is contemplated that the source electromagnetic radiation may include any number of distinct substantially monochromatic wavelengths (e.g., three, four, etc.) or may comprise a spectrum of wavelengths. In some embodiments, the source electromagnetic radiation comprises a broadband source of electromagnetic radiation. The source electromagnetic radiation may be polarized. The source electromagnetic radiation from the radiation source 330 (FIG. 3) may be transmitted through the at least one fiber optic cable to the distal tip of the catheter 200.

As described above, at least a portion of the source electromagnetic radiation transmitted to the distal tip 210 (FIG. 3) of the fiber optic cable 206 (FIG. 3) may be absorbed by one or more of the blood, vascular walls, or tissue proximate the distal tip 210 and at least another portion of the source electromagnetic radiation may be scattered, reflected, or both by one or more of the blood, vascular walls, or the tissue proximate the distal tip 210. At operation 808, at least one of a spectrum, an intensity, or a reflectance of the backscattered electromagnetic radiation may be detected by the detector. In some embodiments, the detector is coupled to the fiber optic cable and the backscattered electromagnetic radiation is transmitted to the detector through the fiber optic cable. Measuring a spectrum of the backscattered electromagnetic radiation may include determining a shift in a peak wavelength between the source electromagnetic radiation and the backscattered electromagnetic radiation. Due to attenuation and backscattering of the electromagnetic radiation in the blood, the reflected electromagnetic radiation may exhibit a spectrum and an intensity that is different than a spectrum and an intensity of the source electromagnetic radiation. Act 808 may include measuring at least one of a spectrum, an intensity, or a reflectance of the backscattered electromagnetic radiation of at least the first substantially monochromatic wavelength and measuring at least one of an intensity or a reflectance of backscattered electromagnetic radiation of at least the second substantially monochromatic wavelength may be measured through the fiber optic cable.

At operation 810, a ratio of an intensity of backscattered electromagnetic radiation of at least the first substantially monochromatic wavelength to an intensity of backscattered electromagnetic radiation of at least the second substantially monochromatic wavelength is determined, as described above with reference to Equation (2).

In addition, or as an alternative approach, operation 810 may include measuring a spectrum of an intensity of the backscattered electromagnetic radiation and determining a ratio of at least an intensity of the backscattered electromagnetic radiation at a first wavelength or between a range of wavelengths to an intensity of the backscattered electromagnetic radiation at a second wavelength or a second range of wavelengths.

In some embodiments, such as where the at least a first substantially monochromatic wavelength is between about 450 nm and about 650 nm and the at least a second substantially monochromatic wavelength is between about 750 nm and about 950 nm, the value of the ratio may decrease as the distal tip of the catheter 200 transitions from the vasculature having a first type of tissue having a first color (e.g., from the veins and the superior vena cava) to a region of the vasculature having a different type of tissue having a different color (e.g., to the cavoatrial junction and the right atrium). At operation 812, the ratio is used to determine a location of the distal tip of the catheter. By way of nonlimiting example, when the distal tip approaches the cavoatrial junction, the ratio may approach a value of about 1.0. For example, and referring again to FIG. 5B through FIG. 5E, the amount of electromagnetic radiation reflected (i.e., backscattered) in the vasculature (e.g., the superior vena cava) may differ significantly between relatively shorter wavelengths (e.g., about 450 nm to about 650 nm) and relatively longer wavelengths (e.g., about 750 nm to about 950 nm) whereas the amount of electromagnetic radiation reflected by the tissue in the heart is relatively similar at the shorter wavelengths and the longer wavelengths. Accordingly, when the distal tip approaches or enters the cavoatrial junction, the ratio may approach a value of about 1.0. In some embodiments, the distal tip may be advanced until the value of the ratio is equal to between about 0.8 and about 1.2, such as between about 0.9 and about 1.1, for example. In other embodiments, the distal tip may be advanced until the value of the ratio is equal to between about 0.55 to about 0.65. Of course, the value of the ratio may depend on one or more of system variables, such as the power of the radiation source 330 (FIG. 3), on system noise, or on the selected wavelengths of source electromagnetic radiation.

In yet other embodiments, the location of the distal tip 210 may be determined based on a rate of change of the value of the ratio. By way of nonlimiting example, the value of the ratio may change more rapidly as the distal tip approaches the cavoatrial junction. In some embodiments, if the value of the ratio changes by at least about 5 percent, at least about 10 percent, at least about 20 percent, at least about 30 percent, at least about 40 percent responsive to advancing or retracting the catheter by about 1 mm, the distal tip may be proximate the cavoatrial junction.

Accordingly, operation 812 includes determining whether the ratio is between a range of predetermined values, if the ratio is changing at greater than a predetermined rate, or both. If the ratio is not between the range of predetermined values, is not changing at greater than a predetermined rate, or both, the method 800 proceeds to operation 814, where the catheter 200 is further advanced through the vascular system. If an intensity of backscattered electromagnetic radiation decreases at one or more wavelengths as the catheter is advanced, the catheter may have undesirably entered a vein and may be traveling away from the CAJ 114 (FIG. 1). In some such embodiments, the catheter may be at least partially retracted prior to continuing advancement thereof.

Operations 806, 808, 810, 812, and 814 may be repeated until the ratio falls within a predetermined range of values, the ratio changes by a predetermined amount, or both, at which point, the method 800 proceeds to operation 816 where the advancement of the catheter is stopped.

Operation 818 includes removing the fiber optic cable from the catheter after the catheter has successfully been placed in the patient.

Although the method 800 has been described as including a first substantially monochromatic wavelength and at least a second substantially monochromatic wavelength, the disclosure is not so limited. For example, the method may include transmitting electromagnetic radiation exhibiting any number of discrete substantially monochromatic wavelengths (e.g., two, three, four, etc.). In some embodiments, at least a third substantially monochromatic wavelength may be transmitted by the radiation source. In some such embodiments, an intensity of backscattered electromagnetic radiation may be measured at the at least a third substantially monochromatic wavelength. The method 800 may include determining a ratio of the intensity of the backscattered electromagnetic radiation at the at least a third substantially monochromatic wavelength to at least one of the intensity of the backscattered electromagnetic radiation at the at least a first substantially monochromatic wavelength or the intensity of the backscattered electromagnetic radiation at the at least a second monochromatic wavelength. Of course, it is contemplated that any number of discrete substantially monochromatic wavelengths may be transmitted from the radiation source 330 (FIG. 3) and an intensity any number of discrete substantially monochromatic wavelengths may be measured by the detector 340 (FIG. 4) to determine any number of ratios of backscattered electromagnetic radiation may be determined. In some embodiments, calculating more than one ratio may increase an accuracy of the method 800.

As described above, the source electromagnetic radiation transmitted to the distal tip of the fiber optic cable may exhibit a frequency between about 3 KHz and about 50 KHz. Accordingly, although FIG. 7 and FIG. 8 illustrate that operations 706 and 806 include transmitting electromagnetic radiation through the fiber optic cable and operations 708 and 808 include measuring at least one of an intensity and a spectrum of the backscattered electromagnetic radiation, during use and operation, the electromagnetic radiation is substantially continuously transmitted through the fiber optic cable and the backscattered electromagnetic radiation is substantially continuously measured by the detector. In other words, the source electromagnetic radiation provided by the radiation source 330 is not necessarily halted when the detector 340 is measuring the backscattered electromagnetic radiation or when the computing system 350 is determining the ratio of the intensity of the source electromagnetic radiation to the intensity of the backscattered electromagnetic radiation.

The systems and methods described herein may be used to determine at least one property of a catheter in a patient, such as a location of the distal tip of a catheter or a direction of motion of the distal tip relative to the cavoatrial junction or to a direction of flow of blood in any anatomy wherein a volume of reflectors, such as red blood cells, changes as the catheter is inserted. For example, the system and methods may be used to determine a location of the distal tip of the catheter at locations within the vasculature exhibiting an increase (or similarly, a decrease) in cross-sectional area. However, the disclosure is not limited to determining a location of the distal tip only based on a change in cross-sectional area. In some embodiments, it is contemplated that a volume of reflectors may increase while a cross-sectional area of the vasculature remains substantially constant. In some such embodiments, a concentration of reflectors may be different at one or more locations having substantially the same cross-sectional area in the vasculature, which locations may be determined based on an intensity of electromagnetic radiation backscattered by the reflectors. By way of non-limiting example, a concentration of one or more types of reflectors may vary depending on a proximity to one or more organs or glands.

Accordingly, in some embodiments, the systems and methods described herein may be used to determine and/or provide a signal indicative of one or more properties of a catheter within the vasculature of a patient. The methods may include a method of determining and/or providing a signal indicative of one or more properties of a catheter in the vasculature of a patient based on, or based at least in part on, a ratio of an intensity of backscattered electromagnetic radiation from the vasculature of a first wavelength to an intensity of the backscattered electromagnetic of at least a second wavelength (i.e., $R_b$ (Equation (2)) or otherwise on a spectrum of the backscattered radiation, a method of determining and/or providing a signal indicative of one or more properties of a catheter in the vasculature of a patient based on, or at least in part on, an intensity of backscattered radiation and for example a ratio of an intensity of source electromagnetic radiation to an intensity of backscattered electromagnetic radiation (i.e., $R_I$ (Equation (1)), or both. The systems may include a system for determining and/or providing a signal indicative of one or more properties of a catheter in the vasculature of a patient based on, or based at least in part on, a ratio of an intensity of backscattered electromagnetic radiation from the vasculature of a first wavelength to an intensity of the backscattered electromagnetic of at least a second wavelength (i.e., $R_b$ (Equation (2)) or otherwise on a spectrum of backscattered radiation, a system for determining and/or providing a signal indicative of at least one property of a catheter in the vasculature of a patient based on, or at least in part on, an intensity of backscattered radiation and for example a ratio of an intensity of source electromagnetic radiation to an intensity of backscattered electromagnetic radiation (i.e., $R_I$ (Equation (1)), or both. When the system is configured to determine both ratios, $R_I$ and $R_b$, or to otherwise provide signals indicative of a catheter location or other property based on both backscattered electromagnetic radiation intensity and a spectrum of backscattered electromagnetic radiation (e.g. compared to the source intensity or spectrum), the system may be configured to provide a separate audible and/or visual indication to a user (e.g., a clinician) based on these parameters, e.g. a first audible and/or visible indication based on a value of $R_I$ and a second, separate audible and/or visual indication to the user based on the value of $R_b$. In some embodiments, the system may further be configured to provide a separate audible and/or visual indication to the user responsive to determining a direction of blood flow relative to the distal tip of the catheter. In some such embodiments, the system may be configured to provide different audible and visual signals based on the direction of the blood flow relative to the distal tip. Accordingly, the method may include providing a separate audible and/or visual indication to a user based on a value of $R_I$, a separate audible and/or visual indication to the user based on the value of $R_b$, and a separate audible and/or visual indication based on the direction of blood flow relative to the distal tip. It will be understood, however, that these various backscattered electromagnetic radiation signals, potentially in relation to their electromagnetic radiation source or sources, can also be assessed together by the processor in the system, to generate a single audible and/or visual indication to a user indicative of a property of a catheter (e.g. catheter tip location). These considerations for processing the backscattered signal or signals from within the vasculature of the patient can be used in all embodiments disclosed herein unless otherwise expressly indicated or clear in context.

Accordingly, one or more properties of a catheter (e.g. the catheter tip location) may be determined and/or a visible or audible signal may be provided to a user during a time period in which the catheter is moved through (e.g., advanced or retracted longitudinally in) the vasculature of a patient. In some such embodiments, the source electromagnetic radiation, detection of one or more properties of the backscattered electromagnetic radiation (e.g., an intensity thereof, a spectrum thereof, an intensity at one or more wavelengths thereof), and a signal indicative of one or more properties of the catheter (e.g., a location thereof) may be provided during the time period in which the catheter is moved through (e.g., advanced or retracted longitudinally in) the vasculature of a patient. These considerations for backscattered signal generation and subsequent steps or processing can be used in all embodiments disclosed herein unless otherwise expressly indicated or clear in context.

Additional non-limiting example embodiments of the disclosure are set forth below.

Embodiment 1: A method of determining a location of a distal tip of a catheter relative to a cavoatrial junction, the method comprising: inserting a catheter into a vein of a patient to a location approaching the cavoatrial junction of the patient; the catheter comprising at least one optical fiber extending from a proximal end of the catheter to a location proximate a distal tip of the catheter; the at least one optical fiber operably coupled at a proximal end thereof to a radiation source configured to transmit electromagnetic radiation through the at least one optical fiber and to the distal tip of the catheter; the at least one optical fiber operably coupled at the proximal end thereof to a detector configured to measure an intensity of electromagnetic radiation; transmitting source electromagnetic radiation at an intensity from the radiation source through the at least one optical fiber to a distal tip thereof into blood located proximate the distal tip of the at least one optical fiber; detecting an intensity of backscattered electromagnetic radiation reflected from the blood located proximate the distal tip of the optical fiber; and determining a ratio of the intensity of the source electromagnetic radiation to the intensity of the backscattered electromagnetic radiation.

Embodiment 2: The method of Embodiment 1, further comprising stopping advancement of the catheter responsive to determining that the ratio is less than a predetermined value.

Embodiment 3: The method of Embodiment 2, further comprising selecting the predetermined value to be one of less than about 5, less than about 3, or less than about 2.

Embodiment 4: The method of any one of Embodiments 1 through 3, further comprising selecting the at least one optical fiber to comprise at least a first optical fiber coupled to the radiation source and at least a second optical fiber coupled to the detector.

Embodiment 5: The method of any one of Embodiments 1 through 4, wherein transmitting source electromagnetic radiation at an intensity from the radiation source comprises transmitting electromagnetic radiation exhibiting a wavelength in a near-infrared region of the electromagnetic spectrum.

Embodiment 6: The method of any one of Embodiments 1 through 5, wherein inserting a catheter into a vein of a patient comprises inserted a catheter comprising the at least one optical fiber in a lumen of the catheter into the vein of the patient.

Embodiment 7: A system for determining a location of a catheter within a patient, the system comprising: at least one optical fiber extending from a proximal end of a catheter to a distal tip of the catheter; a radiation source operably coupled to a proximal end of the at least one optical fiber and configured to transmit source electromagnetic radiation at an intensity through the at least one optical fiber to a distal tip thereof; a detector operably coupled to the proximal end of the at least one optical fiber and configured to measure an intensity of backscattered electromagnetic radiation received at the distal tip of the at least one optical fiber; and a computing system configured to calculate a ratio of the intensity of the source electromagnetic radiation to the intensity of the received electromagnetic radiation.

Embodiment 8: The system of Embodiment 7, wherein the at least one optical fiber comprises a first optical fiber operably coupled to the radiation source and a second optical fiber operably coupled to the detector.

Embodiment 9: The system of Embodiment 7 or Embodiment 8, wherein a distal end of one of the first optical fiber and the second optical fiber is located closer to the distal tip of the catheter than the other of the distal end of the first optical fiber and the second optical fiber.

Embodiment 10: The system of Embodiment 7 or Embodiment 8, wherein a distal end of the first optical fiber and a distal end of the second optical fiber are substantially coincident.

Embodiment 11: The system of any one of Embodiments 7 through 10, wherein the computing system further comprises at least one of an electronic display and a speaker configured to provide an indication when the ratio is less than about 5.

Embodiment 12: A method of determining a location of a distal tip of a catheter relative to a cavoatrial junction, the method comprising: inserting a catheter into a vein of a patient to a location approaching the cavoatrial junction of the patient; the catheter comprising at least one optical fiber extending from a proximal end of the catheter to a location proximate a distal tip of the catheter; the at least one optical fiber operably coupled at a proximal end thereof to a radiation source configured to transmit electromagnetic radiation through the at least one optical fiber and to the distal tip of the catheter; the at least one optical fiber operably coupled at the proximal end thereof to a detector configured to measure an intensity of electromagnetic radiation; transmitting source electromagnetic radiation at an intensity from the radiation source through the at least one optical fiber to a distal tip thereof into blood located proximate the distal tip of the at least one optical fiber; detecting an intensity of backscattered electromagnetic radiation reflected from the blood located proximate the distal tip of the optical fiber; and determining a ratio of the intensity of the source electromagnetic radiation to the intensity of the backscattered electromagnetic radiation.

Embodiment 13: The method of Embodiment 12, further comprising stopping advancement of the catheter responsive to determining that the ratio is less than a predetermined value.

Embodiment 14: The method of Embodiment 13, further comprising selecting the predetermined value to be one of less than about 5, less than about 3, or less than about 2.

Embodiment 15: The method of any one of Embodiments 12 through 14, further comprising selecting the at least one optical fiber to comprise at least a first optical fiber coupled to the radiation source and at least a second optical fiber coupled to the detector.

Embodiment 16: The method of any one of Embodiments 12 through 15, wherein transmitting source electromagnetic radiation at an intensity from the radiation source comprises transmitting electromagnetic radiation exhibiting a wavelength in a near-infrared region of the electromagnetic spectrum.

Embodiment 17: The method of any one of Embodiments 12 through 16, wherein inserting a catheter into a vein of a patient comprises inserting a catheter comprising the at least one optical fiber in a lumen of the catheter into the vein of the patient.

Embodiment 18: The method of any one of Embodiments 12 through 14, 16, and 17, wherein detecting an intensity of backscattered electromagnetic radiation reflected from the blood located proximate the distal tip of the optical fiber comprises detecting the intensity of the backscattered electromagnetic radiation with the same at least one optical fiber from which the source electromagnetic radiation is transmitted.

Embodiment 19: The method of any one of Embodiments 12 through 14, and 16 through 18, wherein the at least one optical fiber comprises a single optical fiber.

Embodiment 20: A system for determining a location of a catheter within a patient, the system comprising: at least one optical fiber extending from a proximal end of a catheter to a distal tip of the catheter; a radiation source operably coupled to a proximal end of the at least one optical fiber and configured to transmit source electromagnetic radiation at an intensity through the at least one optical fiber to a distal tip thereof; a detector operably coupled to the proximal end of the at least one optical fiber and configured to measure an intensity of backscattered electromagnetic radiation received at the distal tip of the at least one optical fiber; and a computing system configured to calculate a ratio of the intensity of the source electromagnetic radiation to the intensity of the received electromagnetic radiation.

Embodiment 21: The system of Embodiment 20, wherein the at least one optical fiber comprises a first optical fiber operably coupled to the radiation source and a second optical fiber operably coupled to the detector.

Embodiment 22: The system of Embodiment 21, wherein a distal end of one of the first optical fiber and the second optical fiber is located closer to the distal tip of the catheter than the other of the distal end of the first optical fiber and the second optical fiber.

Embodiment 23: The system of Embodiment 21 or Embodiment 22, wherein a distal end of the first optical fiber and a distal end of the second optical fiber are substantially coincident.

Embodiment 24: The system of any one of Embodiments 20 through 24, wherein the computing system further comprises at least one of an electronic display and a speaker configured to provide an indication when the ratio is less than about 5.

Embodiment 25: The system of any one of Embodiments 20 through 25, wherein the computing system is further configured to determine at least one of a diameter or a cross-sectional area of a vein proximate the distal tip of the at least one optical fiber.

Embodiment 26: A method of determining a location of a distal tip of a catheter, the method comprising: advancing a catheter in a vein of a patient, the catheter comprising a fiber optic cable comprising a single optical fiber coupled to a radiation source and a detector at a proximal end thereof; transmitting source electromagnetic radiation from the radiation source to the distal end of the single optical fiber; measuring an intensity of backscattered electromagnetic radiation with the single optical fiber; and determining a location of a distal tip of the catheter based, at least in part, on a ratio of an intensity of the source electromagnetic radiation to the intensity of the backscattered electromagnetic radiation.

Embodiment 27: The method of Embodiment 26, further comprising stopping advancement of the catheter when the ratio is less than about 5.

Embodiment 28: The method of Embodiment 26 or Embodiment 27, wherein measuring an intensity of backscattered electromagnetic radiation with the single optical fiber comprises measuring the intensity of the backscattered electromagnetic radiation at substantially the same wavelength as the source electromagnetic radiation.

Embodiment 29: The method of any one of Embodiments 26 through 28, further comprising: determining at least one of a diameter or a cross-sectional area of the vein proximate the distal tip of the catheter based on the ratio; and determining a location of a distal tip of the catheter based, at least in part, on the diameter or the cross-sectional area of the vein proximate the distal tip.

Embodiment 30: The method of any one of Embodiments 26 through 29, wherein transmitting source electromagnetic radiation from the radiation source to the distal end of the single optical fiber comprises transmitted electromagnetic radiation having a wavelength between about 750 nm and about 1,100 nm from the radiation source to the distal end of the optical fiber.

Embodiment 31: A method of determining a location of a distal tip of a catheter relative to a cavoatrial junction, the method comprising: inserting a catheter into a vein of a patient to a location approaching the cavoatrial junction of the patient; the catheter comprising at least one optical fiber extending from a proximal end of the catheter to a location proximate a distal tip of the catheter; the at least one optical fiber operably coupled at a proximal end thereof to a radiation source configured to transmit electromagnetic radiation through the at least one optical fiber and to the distal tip of the catheter; the at least one optical fiber operably coupled at the proximal end thereof to a detector configured to measure an intensity of electromagnetic radiation; transmitting source electromagnetic radiation at an intensity from the radiation source through the at least one optical fiber to a distal tip thereof into blood located proximate the distal tip of the at least one optical fiber; detecting an intensity of backscattered electromagnetic radiation reflected from the blood located proximate the distal tip of the optical fiber; and determining a ratio of the intensity of the source electromagnetic radiation to the intensity of the backscattered electromagnetic radiation.

Embodiment 32: The method of Embodiment 31, further comprising stopping advancement of the catheter responsive to determining that the ratio is less than a predetermined value.

Embodiment 33: The method of Embodiment 32, further comprising selecting the predetermined value to be one of less than about 5, less than about 3, or less than about 2.

Embodiment 34: The method of any one of Embodiments 31 through 33, further comprising selecting the at least one optical fiber to comprise at least a first optical fiber coupled to the radiation source and at least a second optical fiber coupled to the detector.

Embodiment 35: The method of any one of Embodiments 31 through 34, wherein transmitting source electromagnetic radiation at an intensity from the radiation source comprises transmitting electromagnetic radiation exhibiting a wavelength in a near-infrared region of the electromagnetic spectrum.

Embodiment 36: The method of any one of Embodiments 31 through 35, wherein inserting a catheter into a vein of a patient comprises inserting a catheter comprising the at least one optical fiber in a lumen of the catheter into the vein of the patient.

Embodiment 37: The method of any one of Embodiments 31 through 33, 35, and 36, wherein detecting an intensity of backscattered electromagnetic radiation reflected from the blood located proximate the distal tip of the optical fiber comprises detecting the intensity of the backscattered electromagnetic radiation with the same at least one optical fiber from which the source electromagnetic radiation is transmitted.

Embodiment 38: The method of any one of Embodiments 31 through 33 or 35 through 37, wherein the at least one optical fiber comprises a single optical fiber.

Embodiment 39: The method of any one any one of Embodiments 31 through 38, wherein detecting an intensity of backscattered electromagnetic radiation reflected from the blood located proximate the distal tip of the optical fiber comprises determining a shift in a wavelength between the source electromagnetic radiation and the backscattered electromagnetic radiation.

Embodiment 40: A system for determining a location of a catheter within a patient, the system comprising: at least one optical fiber extending from a proximal end of a catheter to a distal tip of the catheter; a radiation source operably coupled to a proximal end of the at least one optical fiber and configured to transmit source electromagnetic radiation at an intensity through the at least one optical fiber to a distal tip thereof; a detector operably coupled to the proximal end of the at least one optical fiber and configured to measure an intensity of backscattered electromagnetic radiation received at the distal tip of the at least one optical fiber; and a computing system configured to calculate a ratio of the intensity of the source electromagnetic radiation to the intensity of the received electromagnetic radiation.

Embodiment 41: The system of Embodiment 40, wherein the at least one optical fiber comprises a first optical fiber operably coupled to the radiation source and a second optical fiber operably coupled to the detector.

Embodiment 42: The system of Embodiment 40 or Embodiment 41, wherein a distal end of one of the first optical fiber and the second optical fiber is located closer to the distal tip of the catheter than the other of the distal end of the first optical fiber and the second optical fiber.

Embodiment 43: The system Embodiment 40 or Embodiment 41, wherein a distal end of the first optical fiber and a distal end of the second optical fiber are substantially coincident.

Embodiment 44: The system of any one of Embodiments 40 through 43, wherein the computing system further comprises at least one of an electronic display and a speaker configured to provide an indication when the ratio is less than about 5.

Embodiment 45: The system of any one of Embodiments 40 through 44, wherein the computing system is further configured to determine at least one or a diameter or a cross-sectional area of a vein proximate the distal tip of the at least one optical fiber.

Embodiment 46: The system of any one of Embodiments 40 through 45, wherein the computing system is further configured to determine a direction of movement of the distal tip of the catheter based, at least in part, on a shift in wavelength between the source electromagnetic radiation and the backscattered electromagnetic radiation.

Embodiment 47: A method of determining a location of a distal tip of a catheter, the method comprising: advancing a catheter in a vein of a patient, the catheter comprising a fiber optic cable comprising a single optical fiber coupled to a radiation source and a detector at a proximal end thereof; transmitting source electromagnetic radiation from the radiation source to the distal end of the single optical fiber; measuring an intensity of backscattered electromagnetic radiation with the single optical fiber; and determining a location of a distal tip of the catheter based, at least in part, on a ratio of an intensity of the source electromagnetic radiation to the intensity of the backscattered electromagnetic radiation.

Embodiment 48: The method of Embodiment 47, further comprising stopping advancement of the catheter when the ratio is less than about 5.

Embodiment 49: The method of Embodiment 47 or Embodiment 48, wherein measuring an intensity of backscattered electromagnetic radiation with the single optical fiber comprises measuring the intensity of the backscattered electromagnetic radiation at substantially the same wavelength as the source electromagnetic radiation.

Embodiment 50: The method of any one of Embodiments 47 through 49, further comprising: determining at least one of a diameter or a cross-sectional area of the vein proximate the distal tip of the catheter based on the ratio; and determining a location of a distal tip of the catheter based, at least in part, on the diameter or the cross-sectional area of the vein proximate the distal tip.

Embodiment 51: The method of any one of Embodiments 47 through 50, wherein transmitting source electromagnetic radiation from the radiation source to the distal end of the single optical fiber comprises transmitted electromagnetic radiation having a wavelength between about 750 nm and about 1,100 nm from the radiation source to the distal end of the optical fiber.

Embodiment 52: The method of any one of Embodiments 47 through 51, wherein measuring an intensity of backscattered electromagnetic radiation with the single optical fiber comprises determining a shift in wavelength between the source electromagnetic radiation and the backscattered electromagnetic radiation.

Embodiment 53: The method of Embodiment 52, further comprising determining a direction of movement of the distal tip of the catheter based on the shift in wavelength between the source electromagnetic radiation and the backscattered electromagnetic radiation.

Embodiment 54: The method of any one of Embodiments 47 through 53, further comprising, responsive to a broadening of a spectrum of the backscattered electromagnetic radiation, determining that the distal tip of the catheter is proximate a junction between at least two veins.

Embodiment 55: A method of determining a location of a distal tip of a catheter, the method comprising: advancing a catheter in a vein of a patient, the catheter comprising a fiber optic cable comprising at least one optical fiber coupled to a radiation source and a detector at a proximal end thereof; transmitting source electromagnetic radiation having at least a first substantially monochromatic wavelength and electromagnetic radiation having at least a second substantially monochromatic wavelength from the radiation source to a distal end of the at least one optical fiber; measuring an intensity of backscattered electromagnetic radiation at the at least a first substantially monochromatic wavelength and at the at least a second substantially monochromatic wavelength; determining a ratio of the intensity of the backscattered electromagnetic radiation at the at least a first substantially monochromatic wavelength to the intensity of the backscattered electromagnetic radiation at the at least a second substantially monochromatic wavelength; and determining a location of a distal tip of the catheter based on a value of the ratio.

Embodiment 56: The method of Embodiment 55, further comprising selecting the at least a first substantially monochromatic wavelength to be between about 450 nm and about 650 nm and selecting the at least a second substantially monochromatic wavelength to be between about 750 nm and about 950 nm.

Embodiment 57: The method of Embodiment 55 or Embodiment 56, wherein measuring an intensity of backscattered electromagnetic radiation at the at least a first substantially monochromatic wavelength comprises determining a reflectance of the source electromagnetic radiation having the at least a first substantially monochromatic wavelength.

Embodiment 58: The method of any one of Embodiments 55 through 57, further comprising: transmitting source electromagnetic radiation having at least a third substantially monochromatic wavelength from the radiation source to the distal end of the at least one optical fiber; and measuring an intensity of backscattered electromagnetic radiation at the at least a third substantially monochromatic wavelength.

Embodiment 59: The method of Embodiment 58, further comprising determining a ratio of the intensity of the backscattered electromagnetic radiation at the at least a third substantially monochromatic wavelength to at least one of the intensity of the backscattered electromagnetic radiation at the at least a first substantially monochromatic wavelength or the intensity of the backscattered electromagnetic radiation at the at least a second monochromatic wavelength.

Embodiment 60: The method of any one of Embodiments 55 through 59, wherein determining a location of a distal tip of the catheter based on a value of the ratio comprises determining that the distal tip of the catheter is in a cavoatrial junction of the patient responsive to determining that the ratio is between about 0.8 and about 1.2.

Embodiment 61: The method of any one of Embodiments 55 through 60, wherein determining a location of a distal tip of the catheter based on a value of the ratio comprises determining that the distal tip of the catheter is in a cavoatrial junction of the patient responsive to an increased rate of change of the value of the ratio responsive to movement of the distal tip.

Embodiment 62: The method of any one of Embodiments 55 through 61, wherein determining a location of a distal tip of the catheter based on a value of the ratio comprises determining that the distal tip of the catheter is at the cavoatrial junction responsive to a change in the ratio of at least about 20 percent.

Embodiment 63: The method of any one of Embodiments 55 through 62, wherein transmitting source electromagnetic radiation having at least a first substantially monochromatic wavelength and electromagnetic radiation having at least a second substantially monochromatic wavelength from the radiation source to a distal end of the at least one optical fiber comprises transmitting the source electromagnetic radiation from a broadband source.

Embodiment 64: The method of any one of Embodiments 55 through 63, wherein measuring an intensity of backscattered electromagnetic radiation at the at least a first substantially monochromatic wavelength and at the at least a second substantially monochromatic wavelength comprises measuring a spectrum of an intensity of the backscattered electromagnetic radiation.

Embodiment 65: The method of any one of Embodiments 55 through 64, further comprising determining that the catheter is moving away from a cavoatrial junction of the patient responsive to an increase in the intensity at the at least a first substantially monochromatic wavelength or an increase in the intensity at the at least a second substantially monochromatic wavelength.

Embodiment 66: A system for determining a location of a catheter within a patient, the system comprising: at least one optical fiber extending from a proximal end of a catheter to a distal tip of the catheter; a radiation source operably coupled to a proximal end of the at least one optical fiber and configured to transmit source electromagnetic radiation comprising at least a first substantially monochromatic wavelength and at least a second substantially monochromatic wavelength through the at least one optical fiber to a distal tip thereof; a detector operably coupled to the proximal end of the at least one optical fiber and configured to measure an intensity of backscattered electromagnetic radiation at the at least a first substantially monochromatic wavelength and at the at least a second substantially monochromatic wavelength received at the distal tip of the at least one optical fiber; and a computing system configured to calculate a ratio of the intensity of the backscattered electromagnetic radiation at the at least a first substantially monochromatic wavelength to the intensity of the backscattered electromagnetic radiation at the at least a second substantially monochromatic wavelength.

Embodiment 67: The system of Embodiment 66, wherein the at least one optical fiber comprises a single optical fiber.

Embodiment 68: The system of Embodiment 66 or Embodiment 67, further comprising at least one of an electronic display or a speaker configured to provide an indication when the ratio is within a predetermined range or has changed more than a predetermined amount responsive to advancement of the catheter within the patient.

Embodiment 69: The system of any one of Embodiments 66 through 68, wherein the computing system is further configured to determine advancement of the distal tip away from the cavoatrial junction responsive to a decrease in an intensity of backscattered electromagnetic radiation at one or more wavelengths.

Embodiment 70: A method of determining a location of a distal tip of a catheter, the method comprising: advancing a catheter in a vein of a patient, the catheter comprising a fiber optic cable comprising a single optical fiber coupled to a radiation source and a detector at a proximal end thereof; transmitting source electromagnetic radiation from the radiation source to a distal end of the at least one optical fiber; measuring an intensity of backscattered electromagnetic radiation; determining a ratio of an intensity of backscattered electromagnetic radiation of at least a first wavelength to an intensity of backscattered electromagnetic radiation of at least a second wavelength; and determining a location of a distal tip of the catheter based on a value of the ratio.

Embodiment 71: The method of Embodiment 70, further comprising determining a direction of movement of the catheter based on a relative increase or decrease of an intensity of the backscattered electromagnetic radiation responsive to movement of the catheter.

Embodiment 72: The method of Embodiment 70 or Embodiment 71, wherein transmitting source electromagnetic radiation comprises transmitting the source electromagnetic radiation from a broadband electromagnetic radiation source.

Embodiment 73: The method of any one of Embodiments 70 through 72, wherein measuring an intensity of backscattered electromagnetic radiation comprises determining an intensity of the backscattered electromagnetic radiation at two or more wavelengths.

Embodiment 74: The method of any one of Embodiments 70; through 73, further comprising determining a spectral pattern of backscattered electromagnetic radiation and determining a location of the distal tip of the catheter based, at least in part, on the spectral pattern of the backscattered electromagnetic radiation.

Embodiment 75: A method of determining one or more properties of a catheter in a patient, the method comprising: advancing a catheter in vasculature of a patient, the catheter coupled to at least one radiation source and at least one detector; transmitting source electromagnetic radiation from the at least one radiation source out of the catheter proximate a distal tip thereof; measuring an intensity of backscattered electromagnetic radiation from the at least one radiation source with the at least one detector; and providing a signal indicative of a location of the distal tip within the vasculature based, at least in part, on the measured intensity of the backscattered electromagnetic radiation.

Embodiment 76: The method of Embodiment 75, wherein providing a signal indicative of a location of the distal tip comprises providing at least one of a visual indication or an audible indication to stop advancement of the catheter.

Embodiment 77: The method of Embodiment 75, wherein providing a signal indicative of a location of the distal tip comprises providing at least one of a visual indication or an audible indication to advance or retract the catheter.

Embodiment 78: The method of any one of Embodiments 75 or 77, further comprising advancing or retracting the catheter based, at least in part on a characteristic of the signal.

Embodiment 79: The method of Embodiment 78, wherein advancing or retracting the catheter based, at least in part, on the measured intensity of the backscattered electromagnetic radiation comprises determining a ratio of an intensity of the source electromagnetic radiation to the intensity of the backscattered electromagnetic radiation.

Embodiment 80: The method of Embodiment 79, further comprising advancing the catheter responsive to determining that the ratio is less than a predetermined value.

Embodiment 81: The method of any one of Embodiments 75 through 80, wherein transmitting source electromagnetic radiation from the at least one radiation source comprises transmitting source electromagnetic radiation having a first substantially monochromatic wavelength and at least a second substantially monochromatic wavelength from the at least one radiation source.

Embodiment 82: The method of any one of Embodiments 75 through 81, wherein transmitting source electromagnetic radiation from the at least one radiation source comprises transmitting source electromagnetic radiation from a broadband radiation source.

Embodiment 83: The method of any one of Embodiments 75 through 82, wherein measuring an intensity of backscattered electromagnetic radiation comprises measuring the intensity of the backscattered electromagnetic radiation from radiation sources of at least a first wavelength and at least a second, different wavelength.

Embodiment 84: The method of Embodiment 83, further comprising selecting the at least a first wavelength to be between about 450 nm and about 650 nm and selecting the at least a second wavelength to be between about 750 nm and about 950 nm.

Embodiment 85: The method of Embodiment 83, further comprising determining a ratio of the measured intensity of the backscattered electromagnetic radiation at the at least a first wavelength to the measured intensity of the backscattered electromagnetic radiation at the at least a second wavelength.

Embodiment 86: The method of Embodiment 85, further comprising determining a location of a distal tip of the catheter based, at least in part, on a value of the ratio.

Embodiment 87: The method of Embodiment 86, wherein determining a location of a distal tip of the catheter based, at least in part, on a value of the ratio comprises determining that the distal tip of the catheter is in a cavoatrial junction of the patient responsive to determining that the ratio is between about 0.8 and about 1.2.

Embodiment 88: The method of Embodiment 83, further comprising measuring an intensity of backscattered electromagnetic radiation from a radiation source of at least a third wavelength.

Embodiment 89: The method of Embodiment 88, further comprising determining a ratio of the measured intensity of the backscattered electromagnetic radiation at the at least a third wavelength to at least one of the measured intensity of the backscattered electromagnetic radiation at the at least a first wavelength or the measured intensity of the backscattered electromagnetic radiation at the at least a second wavelength.

Embodiment 90: The method of any one of Embodiments 75 through 89, further comprising determining that a distal tip of the catheter is in a cavoatrial junction of the patient responsive to an increased rate of change of a ratio of an intensity of the backscattered electromagnetic radiation at a first wavelength to an intensity of the backscattered electromagnetic radiation of a second wavelength responsive to movement of the distal tip.

Embodiment 91: The method of Embodiment 90, further comprising determining that the distal tip of the catheter is at the cavoatrial junction responsive to a change in the ratio of at least about 20 percent.

Embodiment 92: A system for determining one or more properties of a catheter within a patient, the system comprising: at least one radiation source coupled to a catheter and configured to transmit source electromagnetic radiation out of the catheter proximate a distal tip thereof; at least one detector operably coupled to the catheter and configured to measure an intensity of backscattered electromagnetic radiation from the at least one radiation source received at a location proximate the distal tip of the catheter; and a computing system configured to provide a signal indicative of a location of the distal tip of the catheter based, at least in part, on a measured intensity of the backscattered electromagnetic radiation.

Embodiment 93: The system of Embodiment 92, wherein the computing system is further configured to determine a location of the distal tip of the catheter relative to a cavoatrial junction of the patient based, at least in part, on a measured intensity of the backscattered electromagnetic radiation.

Embodiment 94: The system of Embodiment 92 or Embodiment 93, further comprising a single optical fiber coupled to the at least one radiation source and the at least one detector and extending to a location proximate the distal tip.

Embodiment 95: The system of any one of Embodiments 92 through 94, wherein the computing system is configured to determine a ratio of an intensity of the backscattered electromagnetic radiation of at least a first wavelength to an intensity of the backscattered electromagnetic radiation of at least a second wavelength.

Embodiment 96: The system of Embodiment 95, further comprising at least one of a visual electronic display or an audio source configured to provide the signal indicative of a location of the distal tip of the catheter when the ratio is within a predetermined range or has changed more than a predetermined amount responsive to advancement of the catheter within the patient.

Embodiment 97: The system of any one of Embodiments 92 through 96, wherein the computing system is further configured to determine movement of the distal tip away from the cavoatrial junction responsive to a decrease in the measured intensity of the backscattered electromagnetic radiation at one or more wavelengths.

Embodiment 98: The system of any one of Embodiments 92 through 97, wherein the computing system is configured to determine a value of a ratio of an intensity of the source electromagnetic radiation to the measured intensity of the backscattered electromagnetic radiation and determine the relative location of the distal tip of the catheter based on the value of the ratio.

Embodiment 99: The system of Embodiment 98, wherein the computing system is configured to determine that the distal tip of the catheter is proximate a cavoatrial junction of the patient responsive to determining that the ratio is less than a predetermined value.

Embodiment 100: A method of determining one or more properties of a catheter in a patient, the method comprising: advancing a catheter in vasculature of a patient, the catheter coupled to at least one radiation source and at least one detector; transmitting source electromagnetic radiation from the at least one radiation source to and out of a distal tip of the catheter; measuring an intensity of backscattered electromagnetic radiation from the at least one radiation source with the at least one detector; and at least one of: determining at least one property of the catheter based, at least in part, on the measured intensity of the backscattered electromagnetic radiation; and visually displaying the measured intensity of the backscattered electromagnetic radiation.

Embodiment 101: The method of Embodiment 100, wherein determining at least one property of the catheter based, at least in part, on the measured intensity of the backscattered electromagnetic radiation comprises determining at least one of: a ratio of an intensity of the source electromagnetic radiation to the measured intensity of the backscattered electromagnetic radiation; and a ratio of the intensity of the measured backscattered electromagnetic radiation of a first wavelength to the measured intensity of the backscattered electromagnetic radiation of at least a second wavelength.

Embodiment 102: The method of Embodiment 100 or Embodiment 101, further comprising determining a direction of movement of the catheter based on a relative increase or decrease of the measured intensity of the backscattered electromagnetic radiation responsive to movement of the catheter.

Embodiment 103: The method of any one of Embodiments 100 through 102, wherein transmitting source electromagnetic radiation comprises transmitting the source electromagnetic radiation from a broadband electromagnetic radiation source.

Embodiment 104: The method of any one of Embodiments 100 through 103, wherein measuring an intensity of backscattered electromagnetic radiation comprises determining an intensity of the backscattered electromagnetic radiation at two or more wavelengths.

Embodiment 105: The method of any one of Embodiments 100 through 104, further comprising determining a spectral pattern of backscattered electromagnetic radiation and determining a location of the distal tip of the catheter based, at least in part, on the spectral pattern of the backscattered electromagnetic radiation.

Embodiment 106: The method of any one of Embodiments 100 through 105, further comprising determining a direction of advancement of the catheter relative to a direction of blood flow based, at least in part, on a shift in a wavelength of a peak intensity of the measured backscattered electromagnetic radiation to a wavelength of a peak intensity of the source electromagnetic radiation.

Embodiment 107: A method of determining one or more properties of a catheter in a patient, the method comprising: receiving, at a processor operably coupled to the catheter, an indication of an intensity of source electromagnetic radiation transmitted from an emitter from a location proximate a distal tip of a catheter within vasculature of a patient; receiving, at the processor, an indication of an intensity of backscattered electromagnetic radiation proximate the distal tip as measured by a receiver; and providing a signal indicative of a location of the distal tip of the catheter based, at least in part, on a measured intensity of the backscattered electromagnetic radiation.

Embodiment 108: The method of Embodiment 107, wherein providing a signal indicative of a location of the distal tip of the catheter comprises providing at least one of an audible signal or a visual signal of the location of the distal tip.

Embodiment 109: The method of Embodiment 107 or Embodiment 108, wherein providing a signal indicative of a location of the distal tip of the catheter based, at least in part, on a measured intensity of the backscattered electromagnetic radiation comprises providing a signal to an output device responsive to determining that a ratio of the intensity of the source electromagnetic radiation to the measured intensity of the backscattered electromagnetic radiation is less than a predetermined value.

Embodiment 110: The method of any one of Embodiments 107 through 109, further comprising: determining, with the processor, at least one of: a relative value of the intensity of the source electromagnetic radiation to the measured intensity of the backscattered electromagnetic radiation; and a relative value of the measured intensity of the backscattered electromagnetic radiation of a first wavelength to the measured intensity of the backscattered electromagnetic radiation of at least a second wavelength.

Embodiment 111: The method of Embodiment 110, wherein providing a signal indicative of a location of the distal tip of the catheter based, at least in part, on a measured intensity of the backscattered electromagnetic radiation comprises providing a signal to an output device responsive to determining that a ratio of the measured intensity of the backscattered electromagnetic radiation of the first wavelength to the measured intensity of the backscattered electromagnetic radiation of at least the second wavelength is between about 0.8 and about 1.2.

Embodiment 112: The method of Embodiment 110 or Embodiment 111, further comprising determining, with the processor, that a distal tip of the catheter is at the cavoatrial junction responsive to a change in a ratio of the measured intensity of the backscattered electromagnetic radiation of the first wavelength to the measured intensity of the backscattered electromagnetic radiation of at least the second wavelength has changed by at least about 20 percent.

Embodiment 113: The method of any one of Embodiments 110 through 112, wherein determining a relative value of the intensity of the source electromagnetic radiation to the measured intensity of the backscattered electromagnetic radiation comprises comparing the measured intensity of the backscattered electromagnetic radiation to values stored in a memory associated with the processor.

Embodiment 114: The method of any one of Embodiments 110 through 113, further comprising determining that the relative value of the intensity of the source electromagnetic radiation to the measured intensity of the backscattered electromagnetic radiation decreases responsive to advancing the catheter from vasculature having a smaller inner diameter to vasculature having a relatively larger inner diameter than the smaller inner diameter.

Embodiment 115: The method of any one of Embodiments 110 through 114, further comprising determining, with the processor, that the distal tip of the catheter is proximate a cavoatrial junction of the patient responsive to determining that a value of a ratio of the measured intensity of the backscattered electromagnetic radiation of the first wavelength to the measured intensity of the backscattered electromagnetic radiation of the at least a second wavelength falls within a predetermined range.

Embodiment 116: The method of any one of Embodiments 107 through 115, further comprising determining, with the processor, that the distal tip of the catheter is proximate a cavoatrial junction of the patient responsive to determining that the relative value of the measured intensity of the backscattered electromagnetic radiation of the first wavelength to the measured intensity of the backscattered electromagnetic radiation of the at least a second wavelength has changed by at least about 20 percent.

Embodiment 117: A system, comprising: a computing system configured to be operably coupled to each of a radiation source and a detector, the computing system comprising: a memory configured to store data related to an intensity of source electromagnetic radiation transmitted from the radiation source and emitted from a distal tip of a catheter; a processor configured to receive an indication of an intensity of backscattered electromagnetic radiation measured by the detector and provide a signal indicative of a location of the distal tip of the catheter based, at least in part, on the measured intensity of the backscattered electromagnetic radiation; and a user interface configured to provide at least one of an audible and a visual indication of the location of the distal tip of the catheter.

Embodiment 118: The system of Embodiment 117, wherein the processor is configured to determine a ratio of the intensity of the source electromagnetic radiation to the measured intensity of the backscattered electromagnetic radiation.

Embodiment 119: The system of Embodiment 117 or Embodiment 118, wherein the processor is further configured to determine a spectrum of the backscattered electromagnetic radiation.

Embodiment 120: The system of any one of Embodiments 117 through 119, wherein the processor is configured to determine at least one of: a relative value of the intensity of the source electromagnetic radiation to the measured intensity of the backscattered electromagnetic radiation; and a relative value of the measured intensity of the backscattered electromagnetic radiation of a first wavelength to the measured intensity of the backscattered electromagnetic radiation of at least a second wavelength.

Embodiment 121: The system of Embodiment 120, wherein the user interface is configured to provide the at least one of an audible and a visual indication of a location of the distal tip of the catheter responsive to at least one of: receiving an indication from the processor that a ratio of the intensity of the source electromagnetic radiation to the measured intensity of the backscattered electromagnetic radiation is less than a predetermined value; and receiving an indication from the processor that a ratio of the measured intensity of the backscattered radiation of the first wavelength to the measured intensity of the backscattered radiation of the at least a second wavelength is within a predefined range.

Embodiment 122: The system of any one of Embodiments 117 through 121, wherein the processor is configured to determine a direction of advancement of the distal tip of the catheter based, at least in part, on a shift in a peak wavelength between the source electromagnetic radiation and a peak wavelength of the backscattered electromagnetic radiation.

Embodiment 123: The system of any one of Embodiments 117 through 122, wherein the processor is configured to determine at least one of a diameter and a cross-sectional area of vasculature proximate the distal tip of the catheter based, at least in part, on the measured intensity of the backscattered electromagnetic radiation.

Embodiment 124: The system of any one of Embodiments 117 through 123, wherein the detector is configured to measure the intensity of the backscattered electromagnetic radiation having a substantially same wavelength as the source electromagnetic radiation.

Embodiment 125: The method of any one of Embodiments 75 through 91 or 107 through 115, wherein said providing a signal indicative of a location of the distal tip within the vasculature is based on the measured intensity of the backscattered electromagnetic radiation.

Embodiment 126: The system of any one of Embodiments 92 through 99, wherein said computing system is configured to provide a signal indicative of a location of the distal tip of the catheter based on a measured intensity of the backscattered electromagnetic radiation.

Embodiment 127: The system of any one of Embodiments 117 through 124, wherein said processor is configured to receive an indication of an intensity of backscattered electromagnetic radiation measured by the detector and provide a signal indicative of a location of the distal tip of the catheter based on the measured intensity of the backscattered electromagnetic radiation.

Embodiment 128: The method of any one of Embodiments 100 through 106, which comprises determining at least one property of the catheter based on the measured intensity of the backscattered electromagnetic radiation.

While the disclosure is susceptible to various modifications and alternative forms, specific embodiments have been shown by way of example in the drawings and have been described in detail herein. However, the disclosure is not intended to be limited to the particular forms disclosed. Rather, the disclosure is to cover all modifications, equivalents, and alternatives falling within the scope of the disclosure as defined by the following appended claims and their legal equivalents.

What is claimed is:

1. A method of determining one or more properties of a catheter in a patient, the method comprising:
   advancing a catheter in vasculature of a patient, the catheter coupled to at least one radiation source and at least one detector;
   transmitting source electromagnetic radiation from the at least one radiation source out of the catheter proximate a distal tip thereof;
   receiving backscattered electromagnetic radiation from the at least one radiation source into an optical fiber within the vasculature and transmitting the backscattered electromagnetic radiation to the at least one detector;

measuring an intensity of the backscattered electromagnetic radiation with the at least one detector; and providing a signal indicative of a location of the distal tip within the vasculature based, at least in part, on the measured intensity of the backscattered electromagnetic radiation;

wherein said providing a signal comprises providing a signal indicative of a location of the distal tip relative to a cavoatrial junction of the patient.

2. The method of claim 1, wherein providing a signal indicative of a location of the distal tip comprises providing at least one of a visual indication or an audible indication to stop advancement of the catheter.

3. The method of claim 1, wherein providing a signal indicative of a location of the distal tip comprises providing at least one of a visual indication or an audible indication to advance or retract the catheter.

4. The method of claim 1, further comprising advancing or retracting the catheter based, at least in part on a characteristic of the signal.

5. The method of claim 4, wherein advancing or retracting the catheter based, at least in part, on the measured intensity of the backscattered electromagnetic radiation comprises determining a ratio of an intensity of the source electromagnetic radiation to the intensity of the backscattered electromagnetic radiation.

6. The method of claim 5, further comprising advancing the catheter responsive to determining that the ratio is less than a predetermined value.

7. The method of claim 1, wherein transmitting source electromagnetic radiation from the at least one radiation source comprises transmitting source electromagnetic radiation having a first substantially monochromatic wavelength and at least a second substantially monochromatic wavelength from the at least one radiation source.

8. The method of claim 1, wherein transmitting source electromagnetic radiation from the at least one radiation source comprises transmitting source electromagnetic radiation from a broadband radiation source.

9. The method of claim 1, wherein measuring an intensity of backscattered electromagnetic radiation comprises measuring the intensity of the backscattered electromagnetic radiation from radiation sources of at least a first wavelength and at least a second, different wavelength.

10. The method of claim 9, further comprising selecting the at least a first wavelength to be between about 450 nm and about 650 nm and selecting the at least a second wavelength to be between about 750 nm and about 950 nm.

11. The method of claim 9, further comprising determining a ratio of the measured intensity of the backscattered electromagnetic radiation at the at least a first wavelength to the measured intensity of the backscattered electromagnetic radiation at the at least a second wavelength.

12. The method of claim 11, further comprising determining the location of the distal tip of the catheter based, at least in part, on a value of the ratio.

13. The method of claim 12, wherein the determining the location of the distal tip of the catheter based, at least in part, on a value of the ratio comprises determining that the distal tip of the catheter is in a cavoatrial junction of the patient responsive to determining that the ratio is between about 0.8 and about 1.2.

14. A method of determining one or more properties of a catheter in a patient, the method comprising:

advancing a catheter in vasculature of a patient, the catheter coupled to at least one radiation source and at least one detector;

transmitting source electromagnetic radiation from the at least one radiation source out of the catheter proximate a distal tip thereof;

measuring an intensity of backscattered electromagnetic radiation from the at least one radiation source with the at least one detector, said measuring an intensity of backscattered electromagnetic radiation comprising measuring the intensity of the backscattered electromagnetic radiation from radiation sources of at least a first wavelength and at least a second, different wavelength;

determining a ratio of the measured intensity of the backscattered electromagnetic radiation at the at least a first wavelength to the measured intensity of the backscattered electromagnetic radiation at the at least a second wavelength; and providing a signal indicative that the distal tip of the catheter is in a cavoatrial junction of the patient responsive to determining that the ratio is between about 0.8 and about 1.2.

15. A method of determining one or more properties of a catheter in a patient, the method comprising:

advancing a catheter in vasculature of a patient, the catheter coupled to at least one radiation source and at least one detector;

transmitting source electromagnetic radiation from the at least one radiation source out of the catheter proximate a distal tip thereof;

measuring an intensity of backscattered electromagnetic radiation from the at least one radiation source with the at least one detector;

providing a signal indicative of a location of the distal tip within the vasculature based, at least in part, on the measured intensity of the backscattered electromagnetic radiation; and wherein said providing a signal comprises providing a signal indicative of a location of the distal tip relative to a cavoatrial junction of the patient.

16. The method of claim 15, wherein said transmitting source electromagnetic radiation from the at least one radiation source comprises transmitting source electromagnetic radiation having a first substantially monochromatic wavelength and at least a second substantially monochromatic wavelength from the at least one radiation source.

* * * * *